United States Patent
Yuan et al.

(10) Patent No.: US 7,544,166 B2
(45) Date of Patent: Jun. 9, 2009

(54) SYSTEMS AND METHODS FOR IMAGING WITH DEPLOYABLE IMAGING DEVICES

(75) Inventors: Jian R. Yuan, Hayward, CA (US); Pei Jie Cao, Fremont, CA (US); Richard Romley, Tracy, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 563 days.

(21) Appl. No.: 11/145,074

(22) Filed: Jun. 3, 2005

(65) Prior Publication Data

US 2006/0276711 A1    Dec. 7, 2006

(51) Int. Cl.
*A61B 8/14* (2006.01)

(52) U.S. Cl. .................. 600/466; 600/459; 600/467; 600/437

(58) Field of Classification Search .................. 600/466, 600/437, 459, 450, 198
See application file for complete search history.

(56) References Cited

U.S. PATENT DOCUMENTS

| | | | |
|---|---|---|---|
| 4,558,706 A | 12/1985 | Nakada et al. |
| 4,802,487 A | 2/1989 | Martin et al. |
| 4,951,677 A | 8/1990 | Crowley et al. |
| 5,000,185 A | 3/1991 | Yock |
| 5,024,234 A | 6/1991 | Leary et al. |
| 5,029,588 A | 7/1991 | Yock et al. |
| 5,178,150 A | 1/1993 | Silverstein et al. |
| 5,190,045 A | 3/1993 | Frazin |
| 5,190,046 A | 3/1993 | Shturman |
| 5,240,003 A | 8/1993 | Lancee et al. |
| 5,331,947 A | 7/1994 | Shturman |
| 5,361,768 A | 11/1994 | Webler et al. |
| 5,372,138 A | 12/1994 | Crowley et al. |
| 5,373,849 A | 12/1994 | Maroney et al. |
| 5,429,136 A | 7/1995 | Milo et al. |
| 5,435,314 A | 7/1995 | Dias |
| 5,437,282 A | 8/1995 | Koger et al. |
| 5,524,630 A | 6/1996 | Crowley |
| 5,546,948 A | 8/1996 | Hamm et al. |
| 5,592,942 A | 1/1997 | Webler et al. |
| 5,598,845 A | 2/1997 | Chandraratna et al. |
| 5,615,682 A | 4/1997 | Stratz, Sr. |
| 5,715,825 A | 2/1998 | Crowley |
| 5,842,994 A | 12/1998 | TenHoff et al. |
| 5,848,969 A * | 12/1998 | Panescu et al. ............... 600/462 |
| 5,938,609 A | 8/1999 | Pomeranz |
| 6,110,121 A | 8/2000 | Lenker |
| 6,120,454 A | 9/2000 | Suorsa et al. |
| 6,165,127 A | 12/2000 | Crowley |
| 6,309,358 B1 | 10/2001 | Okubo |

(Continued)

*Primary Examiner*—Eric F Winakur
*Assistant Examiner*—Katherine L Fernandez
(74) *Attorney, Agent, or Firm*—Darby & Darby P.C.; Patrick R. Turner

(57) ABSTRACT

The systems and methods described herein provide for a medical device insertable into the body of a living being having an imaging device with a layout that is adjustable from an undeployed layout, where the imaging device is insertable into the inner lumen of a medical device, to a larger deployed layout, where the imaging device preferably has a larger imaging aperture. The medical device can also include a flexible membrane coupled with or located on the distal end of the medical device. The flexible membrane can be expanded or inflated to create a spatial operating region for the deployed imaging device.

38 Claims, 17 Drawing Sheets

U.S. PATENT DOCUMENTS

| | | |
|---|---|---|
| 6,364,840 B1 | 4/2002 | Crowley |
| 6,471,648 B1 | 10/2002 | Gamelsky et al. |
| 6,572,553 B2 | 6/2003 | Crowley |
| 6,592,520 B1 | 7/2003 | Peszynski et al. |
| 6,679,845 B2 | 1/2004 | Ritter et al. |
| 6,770,035 B2 * | 8/2004 | White et al. ................ 600/463 |
| 6,780,157 B2 | 8/2004 | Stephens et al. |
| 7,285,117 B2 * | 10/2007 | Krueger et al. ................ 606/34 |
| 2003/0065271 A1 * | 4/2003 | Khoury ....................... 600/509 |
| 2005/0113892 A1 * | 5/2005 | Sproul ........................ 607/100 |
| 2005/0215895 A1 * | 9/2005 | Popp et al. .................. 600/437 |
| 2007/0066902 A1 * | 3/2007 | Wilser et al. ................ 600/459 |

\* cited by examiner

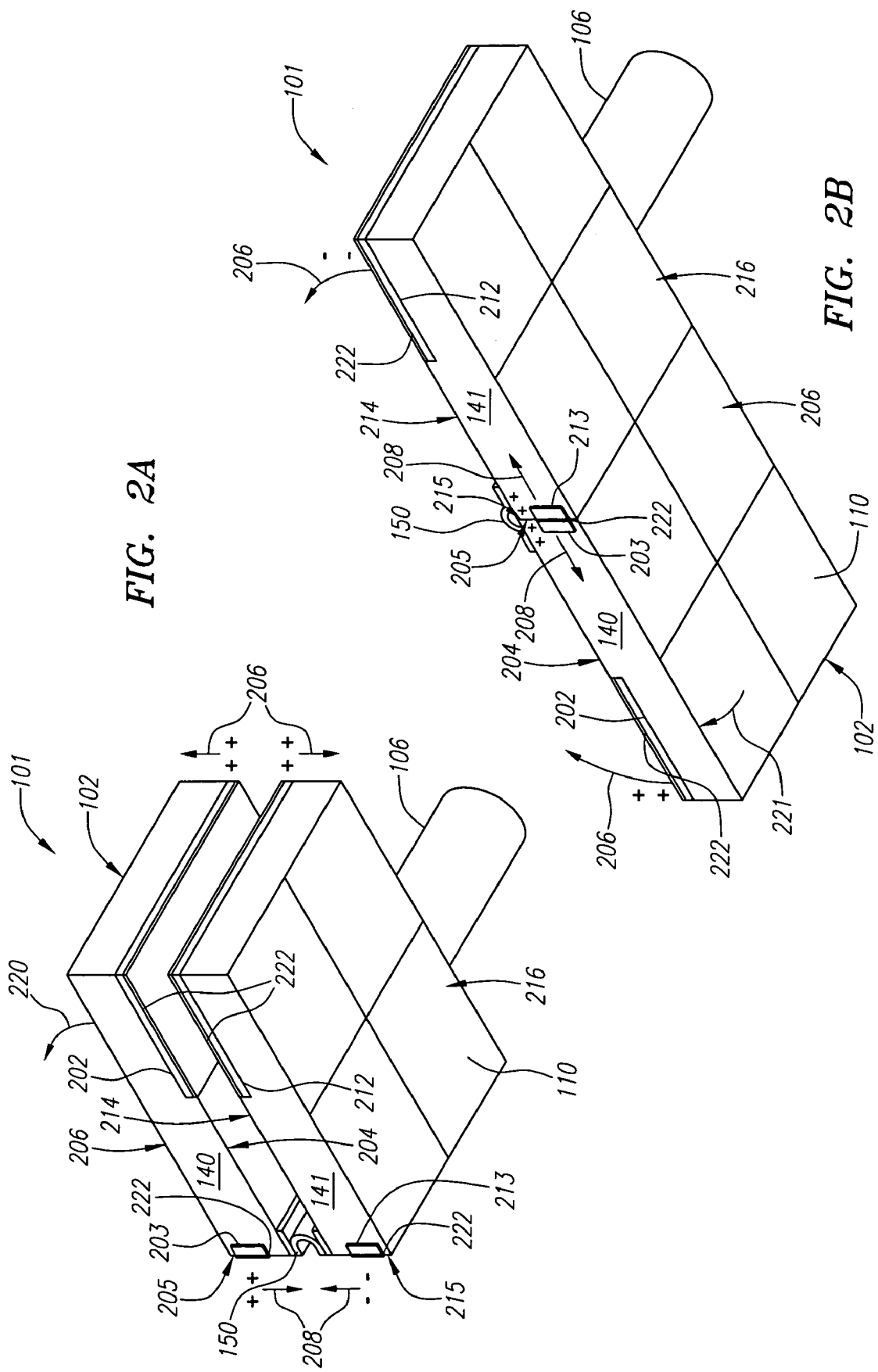

SYSTEMS AND METHODS FOR IMAGING WITH DEPLOYABLE IMAGING DEVICES

FIELD OF THE INVENTION

The systems and methods relate generally to medical ultrasound imaging, and more particularly to imaging with deployable imaging devices.

BACKGROUND INFORMATION

In medical ultrasound imaging systems using a pulse-echo method, the image quality typically depends on the lateral and axial resolution of the imaging beam. The axial resolution is mainly determined by the pulse length, which in turn is mainly determined by the center frequency and bandwidth of the ultrasound imaging device. The lateral resolution is mainly dependent on the aperture size, center frequency and bandwidth of the imaging device. The ultrasound imaging device is typically a single element transducer or transducer array.

For a well focused ultrasound transducer, the beam width ($\beta$) at a focal point is $\beta = f_\# \lambda$, where $f_\#$ is the ratio of the focal depth to the diameter of the aperture and $\lambda$ is the wavelength of the pulse. Thus, an increase in aperture size can allow a narrow beam width to be achieved over a wider range of focal depths. For example, in intracardiac echocardiography (ICE) imaging applications, the target tissue to be imaged could be on the order of 10 centimeters (cm) from the imaging device. Typically, the imaging device must be routed through an artery or other narrow body lumen in order to place the imaging device into proximity with the target tissue. If the desired resolution is one millimeter (mm) and a 10 Megahertz (Mhz) ultrasound frequency is used, the necessary aperture size would be over 10 mm. Conventional imaging devices having an aperture of this magnitude are too large to be delivered into a living being through a catheter and the like.

Accordingly, improved systems and methods are needed, which allow the interior of a living being to be imaged with imaging devices having large apertures.

SUMMARY

The systems and methods described herein provide for an ultrasound imaging system for imaging the interior of a living being with an adjustable imaging device. In one example embodiment, the imaging system can include a medical device having an elongate shaft member and an elongate tubular member configured for insertion into a living being, where the elongate tubular member has an inner lumen adapted to slidably receive the elongate shaft member. The adjustable imaging device is preferably coupled with the shaft member and can be adjustable between a first, undeployed layout and a second, deployed layout. The imaging device is preferably insertable into the inner lumen in the first layout and adapted to image in the second layout.

The imaging device can be further adapted to image in the undeployed layout as well as the deployed layout. The imaging device can be advanced from within the inner lumen by advancing the shaft in a distal direction. Once advanced from the inner lumen, the imaging device can be adjusted to the deployed layout, where the imaging device preferably has a larger aperture than in the first layout. The medical device can also include a flexible membrane coupled with or located at or near the distal end of the elongate tubular member. The flexible membrane is preferably expandable to define a spatial operating region large enough for the imaging device to be deployed within. The membrane is preferably expandable by inflation with an inflation medium such as a fluid, like saline, for example, or a gas, although the membrane can also be expanded or deployed mechanically.

Also provided is a method of imaging with an example embodiment of the imaging system and medical device. In one example method, the medical device, including an imaging device, is advanced within the living being. The imaging device is then adjusted from an undeployed layout to a deployed layout and used to image the living being. The imaging device can also be used to image the living being while the imaging device is in the undeployed layout prior to adjusting the imaging device. A membrane can also be deployed prior to adjusting the imaging device, where the membrane is coupled with the elongate sheath and expandable to define a spatial operating region, into which the imaging device can be advanced and adjusted into the deployed layout.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments.

FIGS. 2A-C are perspective views depicting example embodiments of the medical device.

DETAILED DESCRIPTION

Figure 1A:
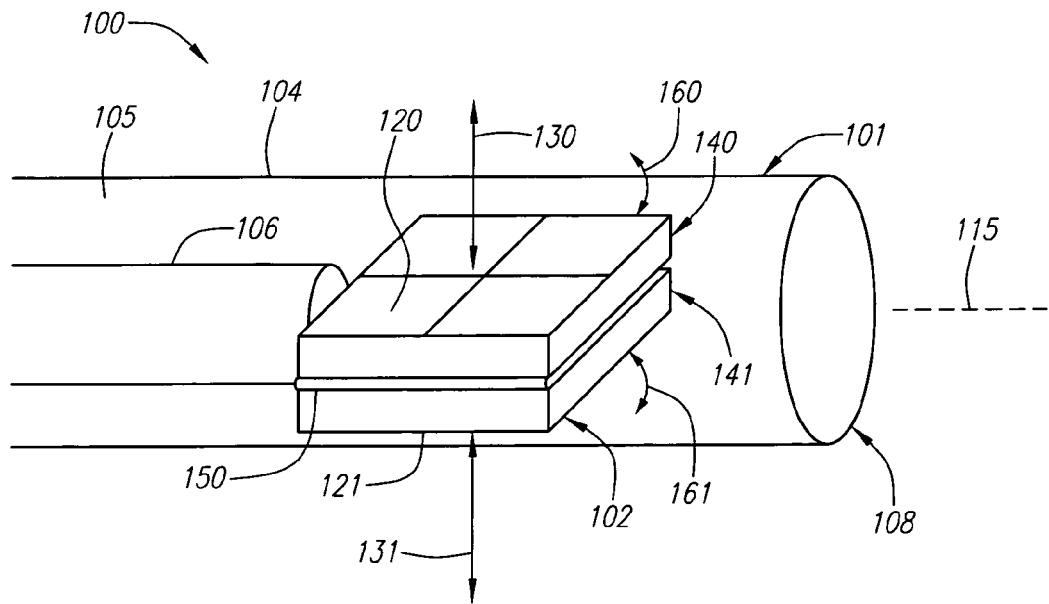
FIGS. 1A-B are perspective views depicting example embodiments of the imaging system.
Figure 1B:
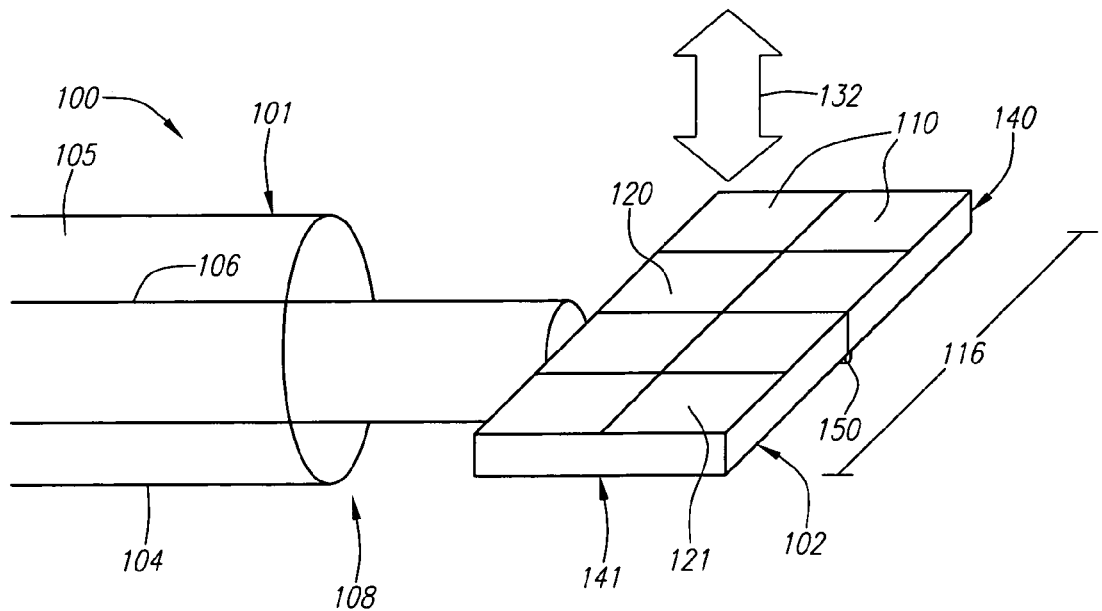

The systems and methods described herein provide for a deployable imaging device for imaging within the body of a living being. FIGS. 1A-B depict example embodiments of an imaging system 100 having a deployable imaging device 102. Here, imaging system 100 includes a medical device 101 adapted for insertion into a living being, such as a catheter, endoscope and the like. In this embodiment, medical device 101 includes an elongate tubular member, or sheath 104 having an inner lumen 105. Imaging device 102 can be coupled with an elongate shaft 106 and adapted to slide proximally and distally within inner lumen 105.

Preferably, imaging device 102 can be adjusted from an undeployed physical configuration, or layout, as depicted in FIG. 1A, where imaging device 102 fits within lumen 105, to a deployed layout as depicted in FIG. 1B, where imaging device 102 has a large imaging aperture for imaging in variable direction 132. In these embodiments, imaging device 102 includes two base structure portions 140 and 141 located side-by-side and preferably coupled together via coupling member 150. Each portion 140 and 141 is adjustable between the undeployed and deployed layouts and back again in directions 160 and 161.

During an imaging procedure, distal end 108 of medical device 101 is inserted percutaneously into the body of a patient, typically through the femoral artery or a similar blood vessel. Medical device 101 is then navigated into proximity with the desired body region to be imaged, e.g., a heart chamber, etc. Once in proximity, shaft 106 can be advanced distally within inner lumen 105 while imaging device 102 is in the undeployed layout. Once imaging device 102 is moved distally past distal end 108, imaging device 102 can be deployed to the layout depicted in FIG. 1B. In the deployed layout, imaging device 102 has a larger, or expanded, layout capable of imaging greater distances within the body. In this embodiment, when in the deployed layout, imaging device 102 has a maximum width 116 measured in a direction perpendicular to the longitudinal axis 115 of elongate sheath 104 that is greater than the width of elongate sheath 104.

Once the imaging procedure is complete, imaging device 102 can be adjusted back to the undeployed layout and retreated proximally back into lumen 105 so that medical device 101 can be withdrawn from the patient. Thus, by adjusting the layout, imaging device 102 can be made small enough to fit within sheath 104, and also large enough to image within the body in a manner not possible for an imaging device sized to image from within sheath 104.

Imaging device 102 is preferably an ultrasound array including one or more ultrasound elements 110 coupled with base structure portions 140 and 141. Imaging device 102 can be any type of array, including, but not limited to a one-dimensional array, a two-dimensional array, a linear array, a phased array and the like. Imaging device 102 can also be arranged in any layout, such as a planar layout, sheet-like layout, umbrella-like layout, foldable layout, coiled layout, or annular layout, to name a few. Example embodiments of imaging device 102 having various different layouts are discussed below.

For ease of discussion, imaging device 102 will be described herein as an array of multiple transducer elements 110. Imaging device 102 and transducer elements 110 can be fabricated in any manner desired. For instance, imaging device 102 can include piezoelectric transducer elements, micromachined ultrasound transducer (MUT) elements such as capacitive micromachined ultrasound transducers (CMUTs) or piezoelectric micromachined ultrasound transducers (PMUTs) and the like.

In the embodiments depicted in FIGS. 1A-B, imaging device 102 is also adapted to image while in the undeployed layout. Transducer elements 110 located on sections 140 and 141 can be used to image in directions 130 and 131, respectively, in order to facilitate navigation through the patient's vasculature or for other diagnostic or therapeutic purposes. Imaging device 102 is preferably communicatively coupled with an image processing system (not shown) and adapted to output one or more signals to the image processing system, the output signals being representative of the imaged region of the body. In one embodiment, communication lines (not shown) are located within shaft 106 and used for communication between the image processing system and imaging device 102. The image processing system is preferably adapted to use the output signals to generate a visual image of the region. As will be discussed below, the image processing system can also be adapted to control the adjustment of imaging device 102 between the deployed and undeployed layouts.

Figure 2C:
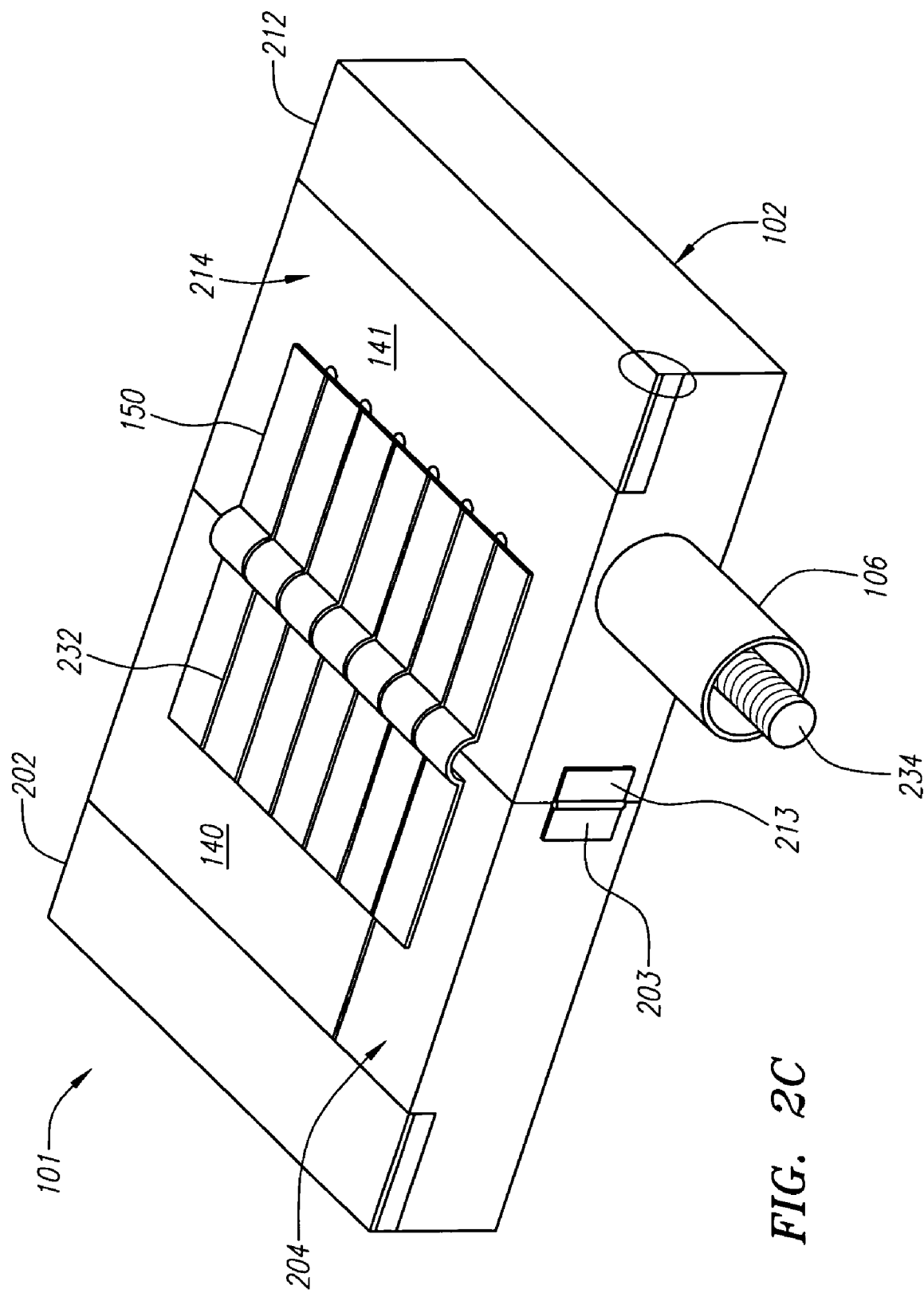

Adjustment of imaging device 102 between the deployed and undeployed layouts can be accomplished in any manner desired. For instance, FIGS. 2A-C depict example embodiments where imaging device 102 is adjustable with the use of electrostatic force. In these embodiments, side portion 140 includes electrodes 202 and 203 and side portion 141 includes electrodes 212 and 213. Portion 140 is preferably coupled with portion 141 via coupling member 150. Here, portion 141 is fixed to shaft 106 and portion 140 is adjustable relative to portion 141. It should be noted that either or both of portions 140 and 141 can be independently adjustable relative to shaft 106.

FIG. 2A depicts imaging device 102 in an undeployed layout where portions 140 and 141 are folded such that back surface 204 of portion 140 is adjacent to back surface 214 of portion 141. Electrodes 202 and 212 are preferably located on back surfaces 204 and 214, respectively, such that an electric charge applied to each electrode can generate an electrostatic force 206 between portions 140 and 141. Electrodes 203 and 213, in turn, are preferably located on side surface 205 of portion 140 and side surface 215 of portion 141, respectively, such that an electric charge applied to each electrode 203 and 213 can generate another, separate electrostatic force 208 between portions 140 and 141.

Each electrode 202, 203, 212 and 213 can be provided with a separate ground wire or any negatively charged electrode can serve as the ground for a positively charged electrode etc. The charge polarity applied to each electrode 202, 203, 212 and 213, determines whether portions 140 and 141 are adjusted from the undeployed layout to the deployed layout or vice versa. In this embodiment, electrodes 202, 203, 212 and 213 are charged to adjust imaging device 102 to the deployed layout.

Here, for instance, electrodes 202 and 212 each have a like charge, in this case positive, resulting in the generation of a repulsive electrostatic force 206 between portions 140 and 141. Conversely, electrodes 203 and 213 have opposite charges, in this case positive and negative charges, respectively, resulting in the generation of an attractive electrostatic force 208 between portions 140 and 141. In this embodiment, each electrode 202, 203, 212 and 213 is preferably covered with an insulative material 222 to prevent excessive charge bleeding or shorts when electrodes 202, 203, 212 and 213 are in close proximity. Preferably, the charges applied to electrodes 202, 203, 212 and 213 are great enough to generate electrostatic forces 206 and 208 having sufficient magnitudes to cause portion 140 to adjust in direction 220 into the deployed layout depicted in FIG. 2B.

In FIG. 2B, side surfaces 205 and 215 are brought together to place front surface 206 of portion 140 and front surface 216 of portion 141 in proximity with each other to form the transducer imaging surface by which ultrasound energy is transmitted and received. Here, imaging device 102 is depicted with electrodes 202, 203, 212 and 213 charged to adjust device 103 to the undeployed layout. Electrodes 202 and 212 each have an opposite charge, in this case positive and negative, respectively, resulting in the generation of an attractive electrostatic force 206 between portions 140 and 141. On the other hand, electrodes 203 and 213 have like charges, in this case positive, resulting in the generation of a repulsive electrostatic force 208 between portions 140 and 141. The combined action of electrostatic forces 206 and 208 can cause portion 140 to adjust in direction 201 back into the undeployed layout.

In the embodiments depicted in FIGS. 2A-B, the electrode pair 202 and 212 are used along with the electrode pair 203 and 213 to adjust imaging device 102. It should be noted that both pairs of electrodes are not required to adjust imaging device 102, and that imaging device 102 can be adapted to utilize only one pair of electrodes in the adjustment process. Furthermore, any number of electrodes can be used to adjust imaging device 102 and, accordingly, the systems and methods described herein is not intended to be limited to the specific number and placement of electrodes described with respect to FIGS. 2A-B.

Coupling member 150 is preferably adapted to allow portion 140 to swing between the deployed and undeployed layouts with relatively little resistance. Coupling member 150 is preferably a flexible member that provides a sufficient degree of rigidity to maintain the proper alignment for portions 140 and 141 when in the deployed layout. FIG. 2C depicts one example embodiment of imaging device 102 where coupling member 150 is a flexible membrane having multiple conductive traces 232. Conductive traces 232 can be routed through portion 140 to communicatively couple transducer elements 110 with the image processing system. Conductive traces 232 can also be coupled with electrodes 202 and 203 to provide charge to electrodes 202 and 203 and traces 232 can also provide any ground connections that are needed. In other embodiments, coupling member 150 can be a combination of rigid members that together allow the desired motion, such as, for instance, a hinge or a pivot and the like, in which case the signal lines can be routed over coupling member 150 or in any other manner in accordance with the needs of the application.

Figure 3A:
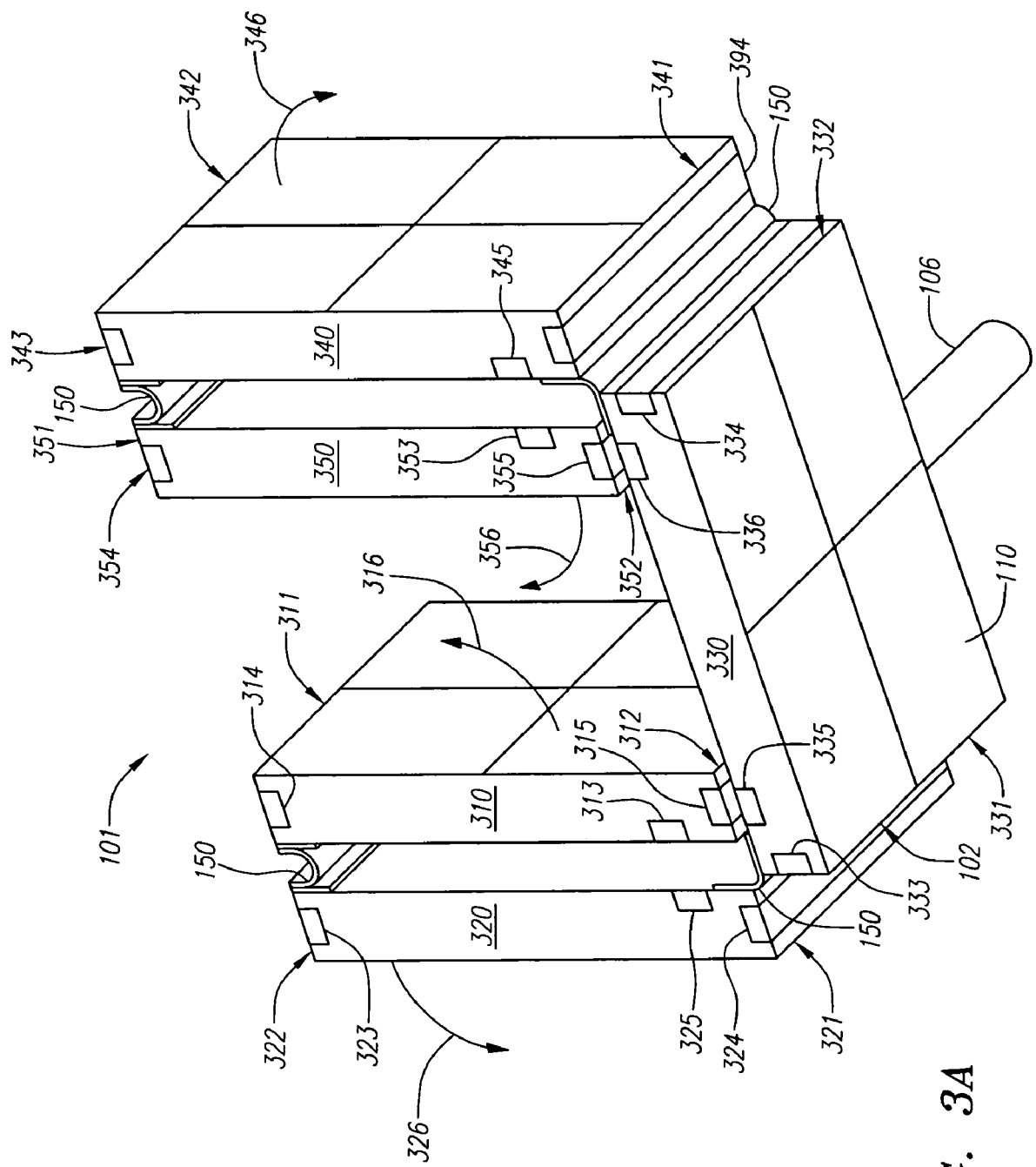
FIGS. 3A-B are perspective views depicting additional example embodiments of the medical device.
Figure 3B:
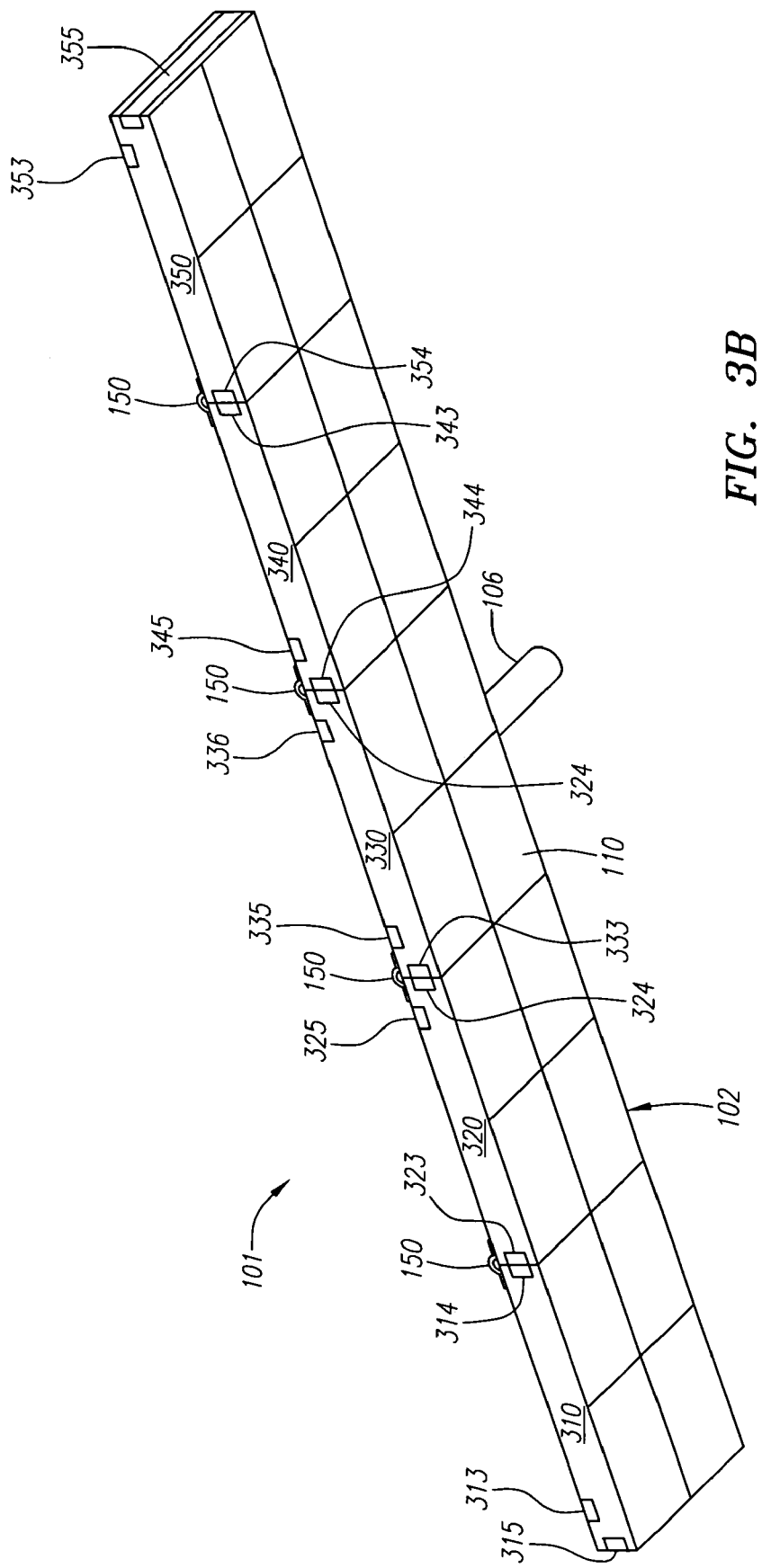

FIGS. 3A-B depict another example embodiment of imaging device 102. In this embodiment, imaging device 102 includes five separate base structure portions 310, 320, 330, 340 and 350, which can be folded up about multiple coupling members 150 to provide a more compact undeployed layout, as depicted in FIG. 3A, as well as a larger imaging aperture 132 in the deployed layout, as depicted in FIG. 3B. Here, each portion has a first side 311, 321, 331, 341 and 351 and a second side 312, 322, 332, 342 and 352, respectively. Side 331 of center portion 330 is coupled with side 321 of portion 320 and side 332 of center portion 330 is coupled with side 341 of portion 340. In turn, side 322 of portion 320 is coupled with side 311 of portion 310 and side 342 of portion 340 is coupled with side 351 of portion 350. Each two portions 310-350 coupled together are preferably done so with coupling member 150. Each portion 310-350 preferably includes one or more imaging elements 110.

Similar to the embodiments described with respect to FIGS. 2A-C, in this embodiment imaging device 102 is adjusted using electrostatic forces generated by electrodes located on each portion 310-350. Here, portion 310 includes electrodes 313, 314 and 315, portion 320 includes electrodes 323, 324 and 325, portion 330 includes electrodes 333, 334, 335 and 336, portion 340 includes electrodes 343, 344 and 345 and portion 350 includes electrodes 353, 354 and 355. Imaging device 102 can then be adjusted between the undeployed layout of FIG. 3A and the deployed layout of FIG. 3B by placing the desired charges on each electrode 313-315, 323-325, 333-336, 343-345 and 353-355 in a manner similar to the embodiments described with respect to FIGS. 2A-B.

For example, to adjust imaging device 102 from the undeployed layout to the deployed layout, portions 320 and 340 are preferably first moved in directions 326 and 346, respectively. Portion 320 can be moved by placing opposite charges on electrodes 324 and 333, while placing like charges on electrodes 315 and 335. Likewise, portion 340 can be moved by placing opposite charges on electrodes 334 and 344, while placing like charges on electrodes 336 and 355. Next, portions 310 and 350 are preferably moved in directions 316 and 356 with respect to portions 320 and 340, respectively. Portion 310 can be moved by placing opposite charges on electrodes 314 and 323, while placing like charges on electrodes 313 and 325 and portion 350 can be moved by placing opposite charges on electrodes 343 and 354, while placing like charges on electrodes 345 and 353. Also, similar to the embodiment discussed with respect to FIG. 2C, imaging signals can be routed to the various elements 110 and charge can be routed to the various electrodes 313-315, 323-325, 343-345 and 353-355 by conductive traces 232 located on each coupling member 150.

It should be noted that imaging device 102 can be adjusted in any manner desired and is not limited solely to adjustment with electrostatic forces. Other example embodiments of imaging device 102 can be adjusted with electrical, mechanical, magnetic and thermal forces, to name a few. For instance, in one example embodiment, imaging device 102 is adjusted to the deployed layout with the aid of a spring member coupled between portions 140 and 141 that applies a force between portions 140 and 141 causing them to adjust to the deployed layout once imaging device 102 is advanced from within sheath 104. Imaging device 102 can then be adjusted back to the undeployed layout using one or more retraction wires coupled with portions 140 and/or 141 or in any other manner desired. Furthermore, the image processing system can be adapted to control the adjustment of imaging device 102 between the various layouts.

Figure 4A:
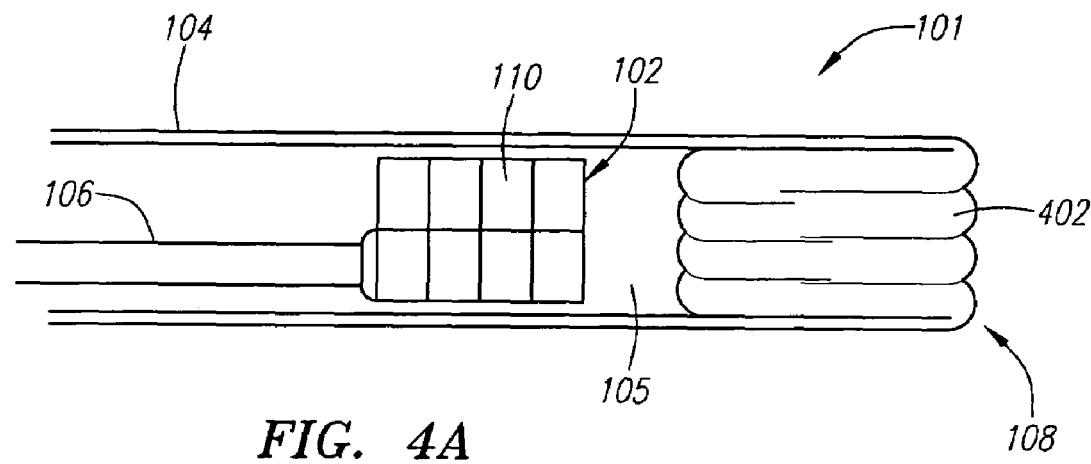
FIGS. 4A-B are cross-sectional views depicting example embodiments of the medical device having a flexible membrane.
Figure 4B:
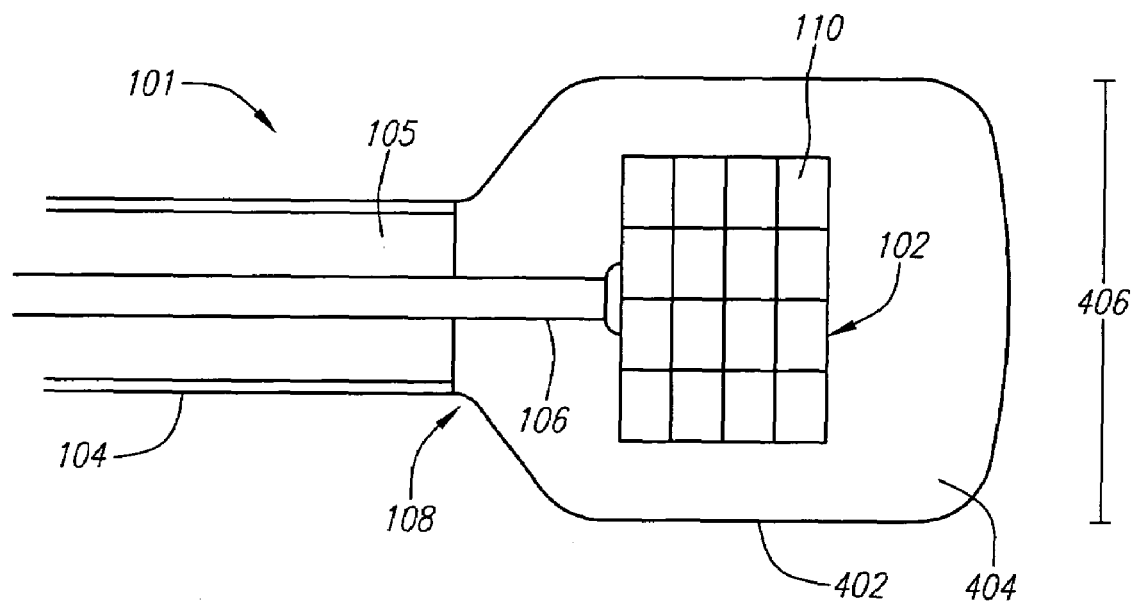

FIGS. 4A-B are schematic views of additional example embodiments where medical device 101 includes membrane 402 located at distal end 108 of elongate sheath 104. Membrane 402 is preferably a thin, flexible layer deployable from within inner lumen 105 and expandable to provide a spatial operating region 404 for imaging device 102. Membrane 402 preferably isolates imaging device 102 to prevent damage or injury to any surrounding body tissue. FIG. 4A depicts membrane 402 in an undeployed position stored within elongate sheath 104. Here, membrane 402 is folded or packed within inner lumen 105 such that membrane 402 does not interfere with the navigation of medical device 101 within the body.

FIG. 4B depicts membrane 402 in a deployed position. In the deployed position, membrane 402 has been advanced distally from within lumen 105 and expanded to define spatial operating region 404 large enough to allow imaging device 102 to be deployed within. Membrane 402 also preferably covers distal end 108 of elongate sheath 104, preventing the escape of fluids from inner lumen 105 and likewise preventing the entrance of blood or other body fluids into lumen 105. The use of membrane 402 also reduces the risk that open distal end 108 will injure, or scive, the interior of the body lumen or chamber.

Membrane 402 can be deployed from lumen 105 using any method in accordance with the needs of the application. Preferably, membrane 402 is inflated with an inflation medium to cause membrane 402 to fill and expand. For instance, in one embodiment, the inflation medium is the fluid, such as saline and the like, that is used to fill inner lumen 105. The fluid pressure within inner lumen 105 is increased until the pressure of the fluid against membrane 402 forces membrane 402 from within lumen 105. Membrane 402 is then filled with the fluid, or inflated, until membrane 402 reaches the desired level of volume expansion. One of skill in the art will readily recognize that any inflation medium can be used including numerous types of fluids and gasses. Membrane 402, when inflated, can have any shape desired. In the example embodiment depicted in FIG. 4B, membrane 402 has a semi-cylindrical shape with a diameter 406 large enough to accommodate imaging device 102.

Figure 5A:
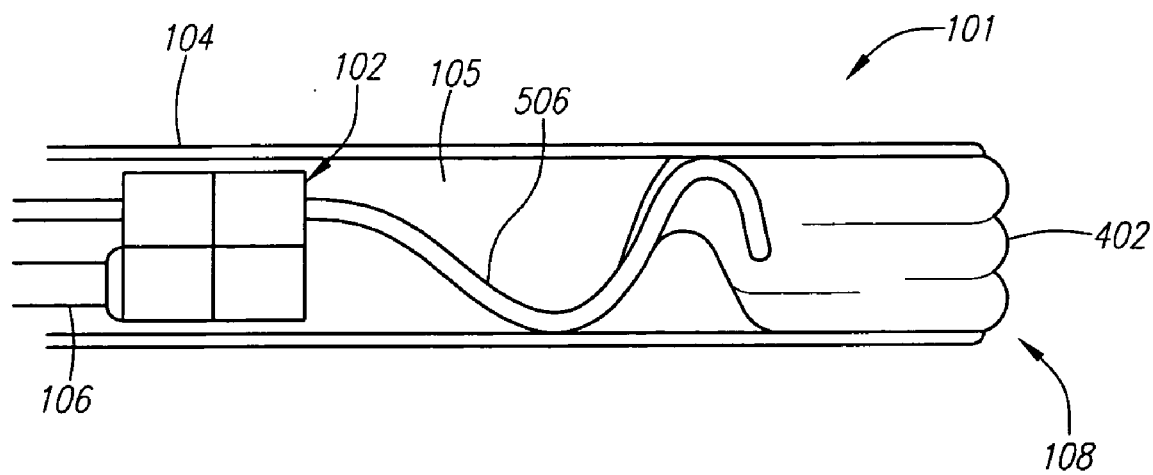
FIGS. 5A-C are cross-sectional views depicting additional example embodiments of the medical device having a flexible membrane.
Figure 5B:
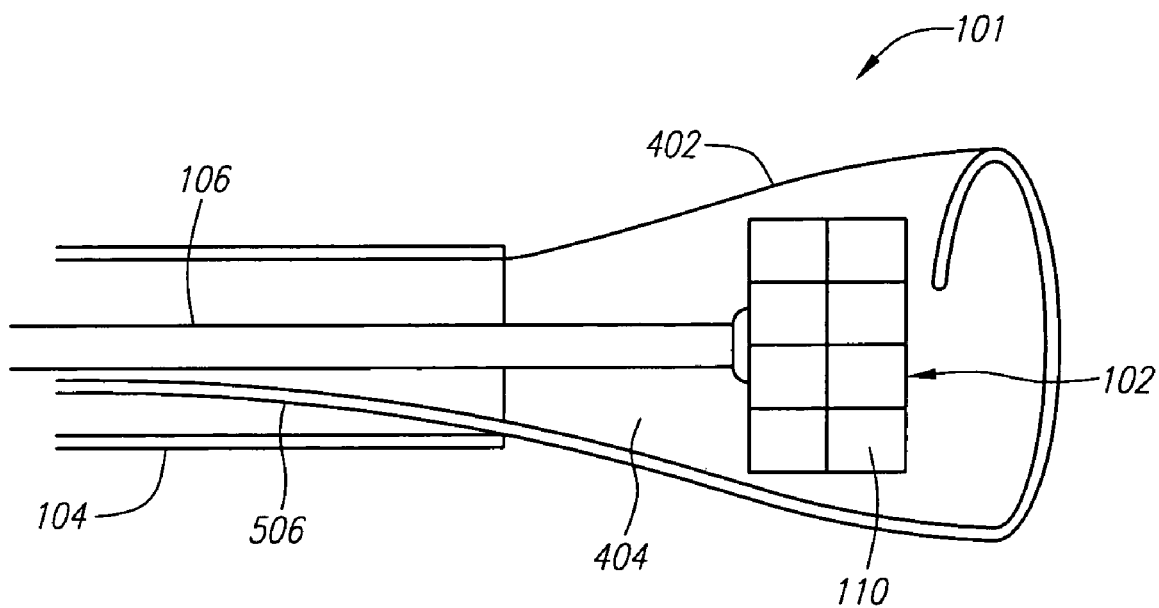
Figure 5C:
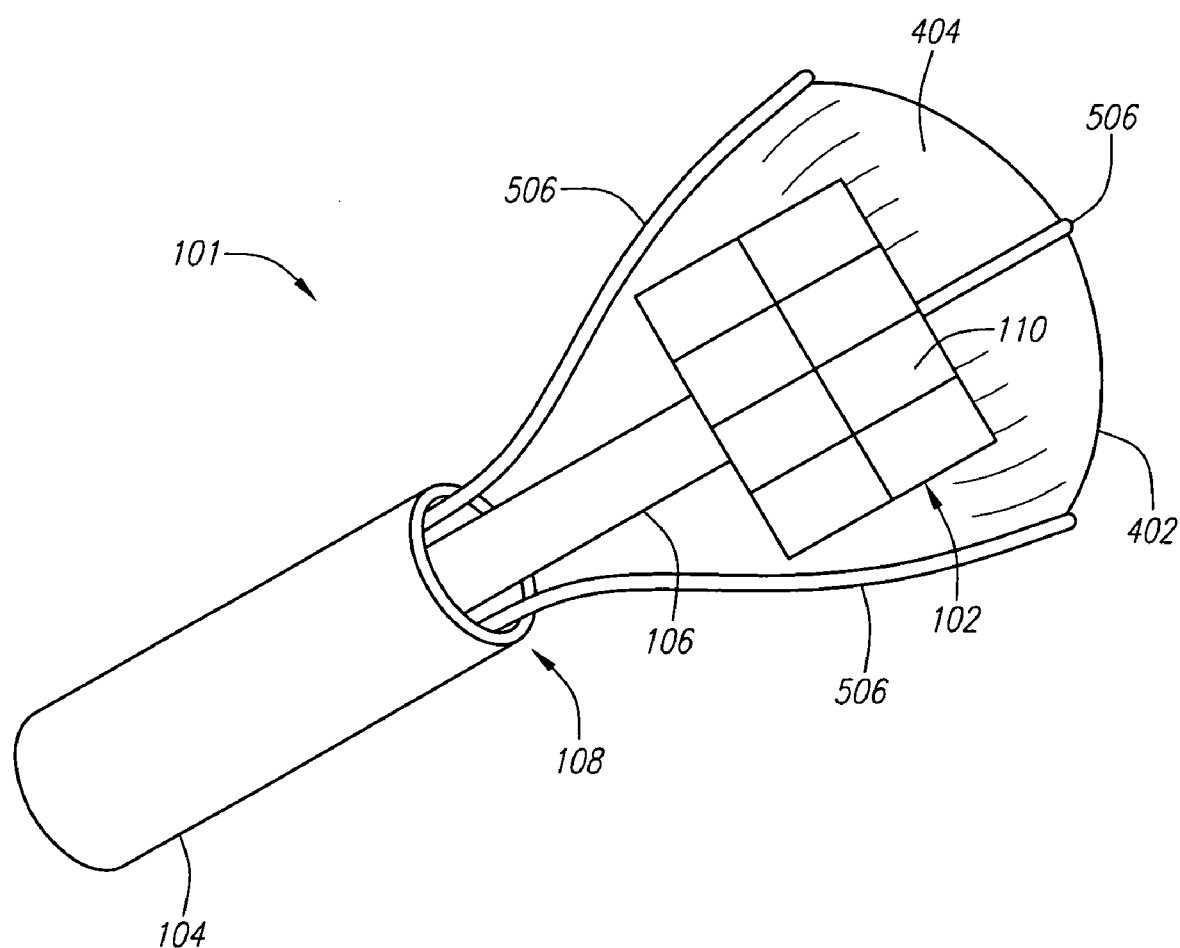

In other embodiments, flexible membrane 402 can be deployed with the aid of one or more physical members. FIGS. 5A-C depict schematic views of additional example embodiments of medical device 101 where one or more mechanical expansion members 506 can be advanced distally from within the sheath 104 to deploy the membrane 402 and hold membrane 402 in an expanded state. FIG. 5A depicts medical device 101 with a single expansion member 506 in a retracted position within sheath 104. FIG. 5B depicts the medical device 101 after expansion member 506 has been advanced distally from within the sheath 104. Expansion member 506 expands and holds membrane 402 in the expanded position once advanced from within sheath 104. Expansion member 506 can be composed of a shape memory material, such as NITINOL, and can be biased towards an expanded position. Expansion member 506 can be coupled with membrane 402 such that membrane 402 will be drawn back into the sheath 104 along with expansion member 506 when the imaging procedure is complete. FIG. 5C depicts another embodiment of medical device 101 where multiple expansion members 506 are employed to expand membrane 402.

Membrane 402 can be fabricated from any material and can have any level of elasticity in accordance with the needs of the application. Examples of materials that can be used to fabricate membrane 402 include, but are not limited to, elastic polymers such as elastomeric polyurethane, silicone polymers, synthetic rubbers such as polyneoprene, neoprene and polybutylene, thermoplastic elastomers and other materials known to those skilled in the art. Membrane 402 can be coupled with the elongate sheath 104 at or near distal end 108. Membrane 402 can be coupled with sheath 104 in any manner, such as with an adhesive, thermal bonding and the like. Membrane 402 can also be fabricated from the same material as sheath 104 such that membrane 402 does not have to be coupled with sheath 104.

Figure 6A:
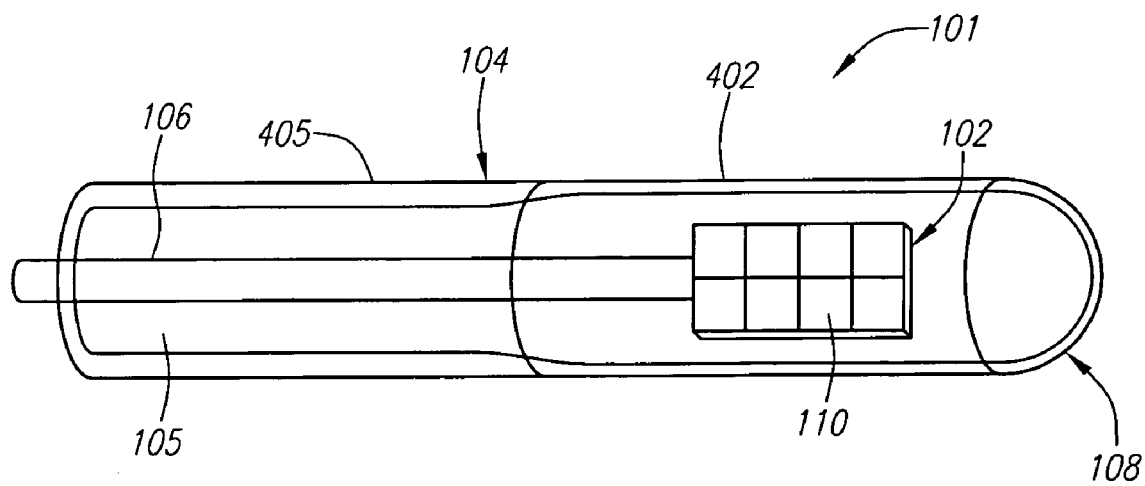
FIGS. 6A-B are cross-sectional views depicting additional example embodiments of the medical device having a flexible membrane.
Figure 6B:
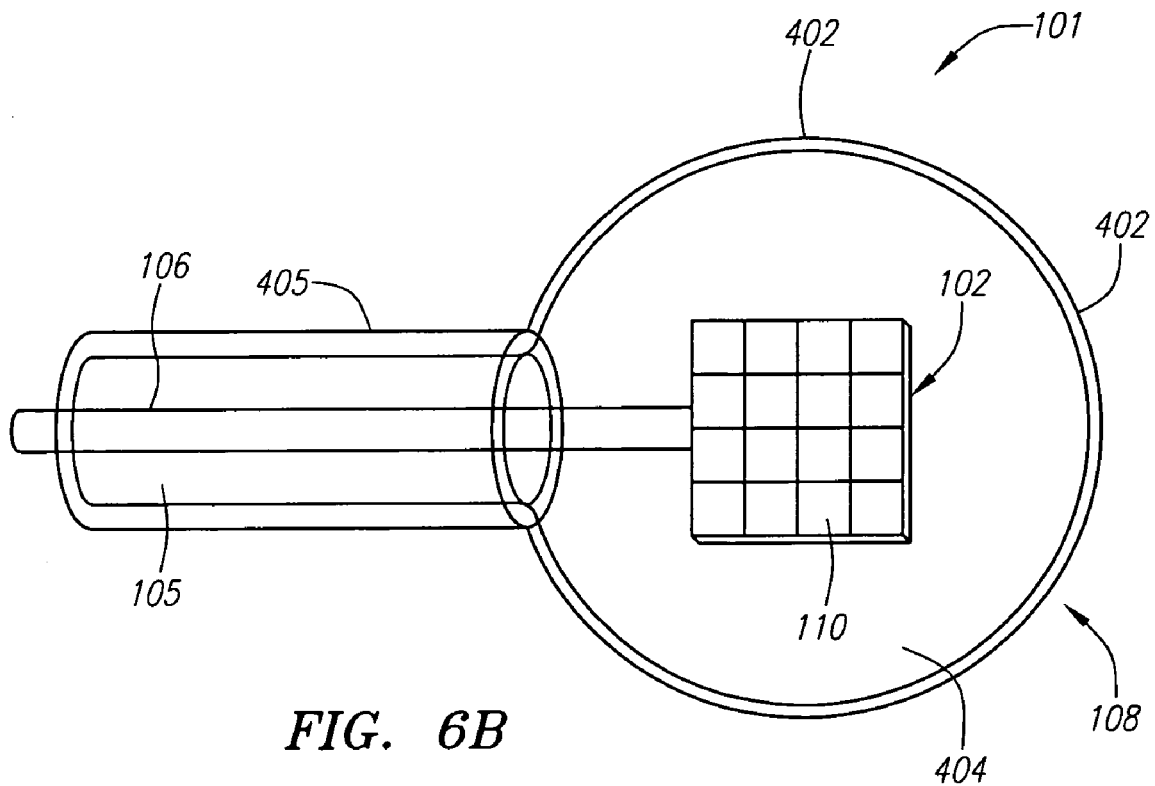

FIGS. 6A-B depict another exemplary embodiment of medical device 101 where membrane 402 is a portion of sheath 104 that is relatively more flexible than the adjacent, proximal portion 405. FIG. 6A depicts membrane 402 prior to deployment. Here it can seen that membrane 402 preferably has the same general shape and size as proximal portion 405 of sheath 104. Similar to the above embodiments, membrane 402 can be deployed through inflation or with the use of one or more mechanical expansion members 506 or in any other manner desired. In this embodiment, membrane 402 is inflated to define spatial operating region 404, as depicted in FIG. 6B. Membrane 402 can be provided with more relative flexibility than portion 404 by using relatively thinner walls to form membrane portion 402 than to form adjacent proximal portion 405 (as shown), by fabricating membrane 402 from a relatively more flexible material than portion 405 or by any other technique desired. Preferably, membrane 402 is flexible enough to allow relatively easy expansion while at the same time being rigid enough to maintain the same general size and shape of sheath 104 when in the unexpanded state.

Figure 7:
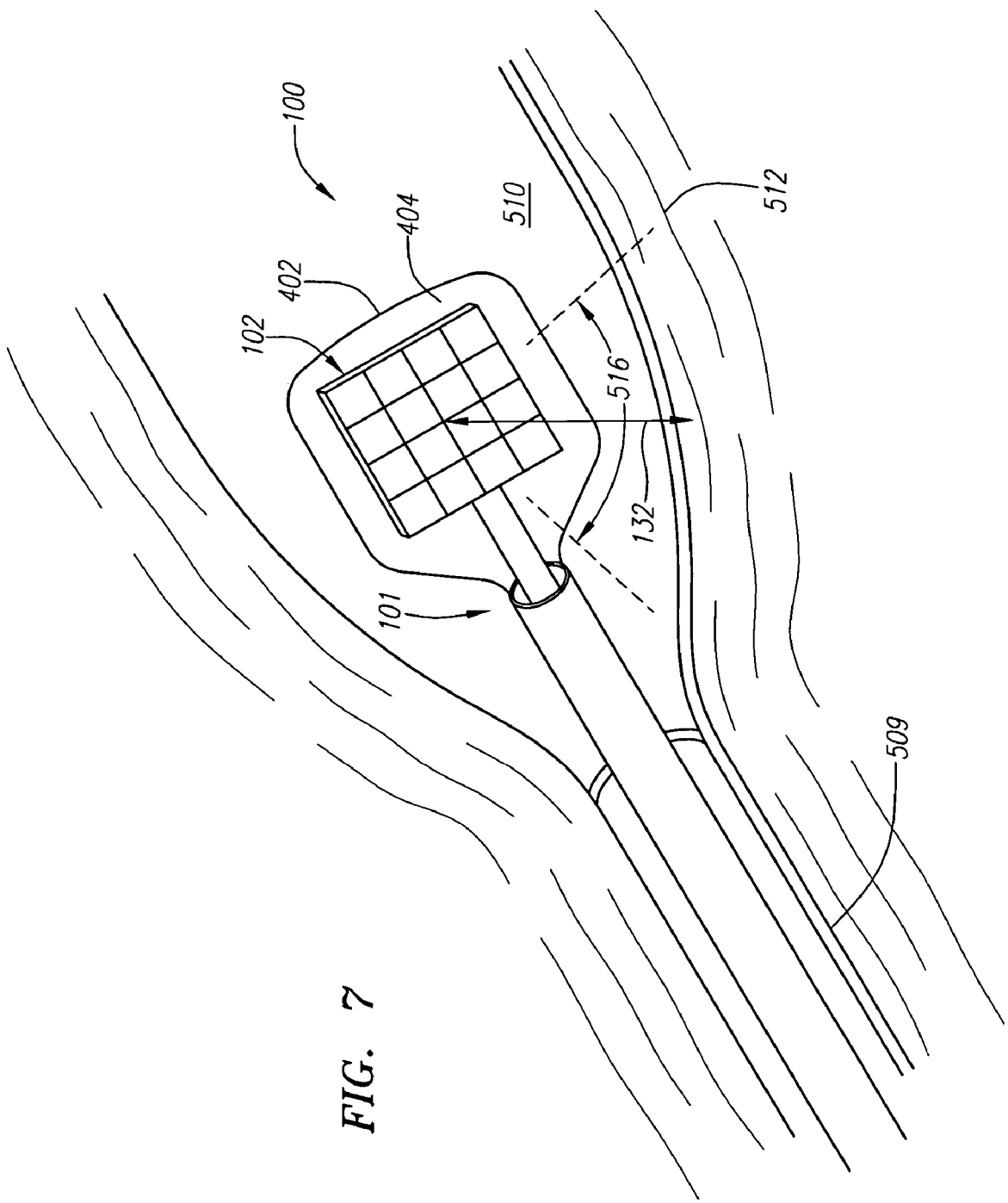
FIG. 7 is a perspective view depicting another example embodiment of the imaging system.

FIG. 7 is a perspective view depicting another example embodiment of medical device 101 within a living being. Here, medical device 101 has been navigated through coronary artery 509 into heart chamber 510, where membrane 402 has been inflated to define spatial region 404 and imaging device 102 has been deployed for imaging within. Imaging device 102 preferably images tissue 408 of heart chamber 406 using an ultrasound pulse-echo technique well known to those of skill in the art. Ultrasound pulses are transmitted from imaging device 102 towards chamber wall tissue 512 in direction 132, which can be any direction within the imaging field 516 of imaging device 102. The echoes generated from the collision of these pulses with tissue 512 are reflected back along direction 132 and received by imaging device 102. Imaging device 102 can be adapted to output one or more signals representative of the strength of the echoes to the image processing system to be used to generate an image of tissue 512. As can be seen from FIG. 7, imaging device 102 in the deployed layout has a larger aperture than in the undeployed layout, which allows imaging device 102 to image a larger imaging field 516 at greater depths.

Figures 8A, 8B:
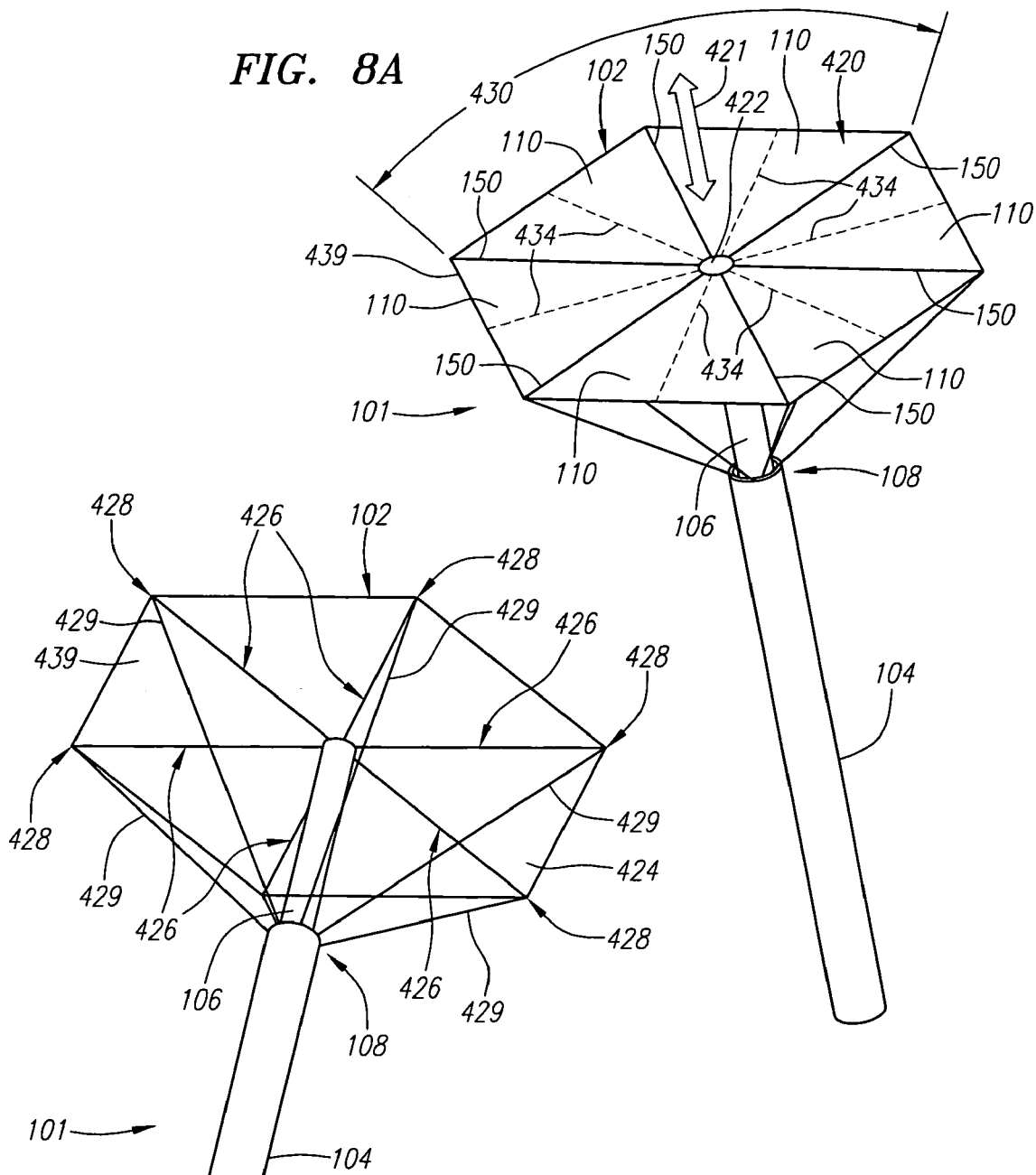
FIGS. 8A-B are perspective views depicting additional example embodiments of the medical device.
Figure 8C:
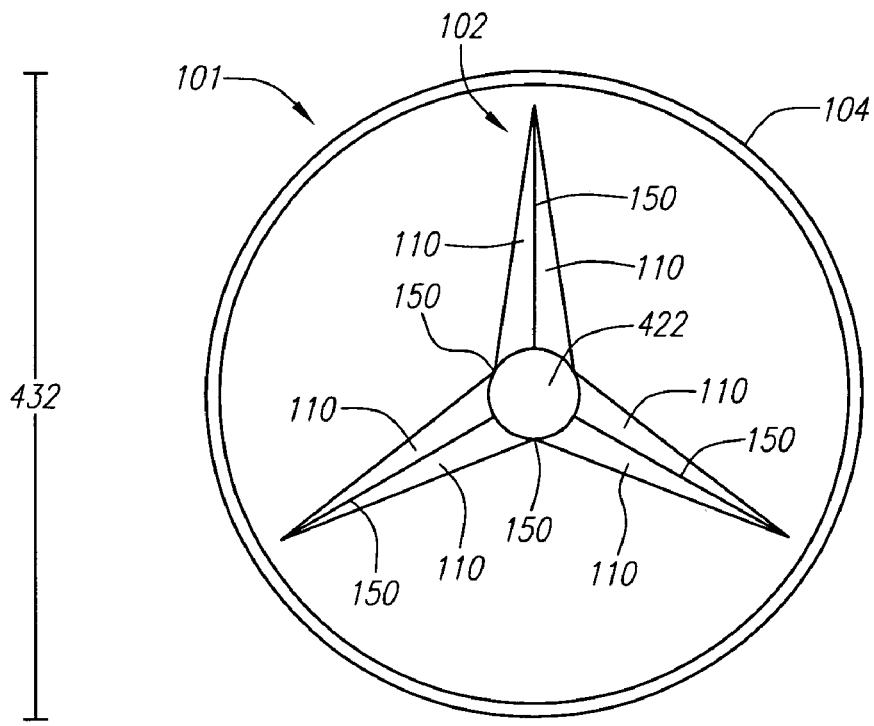
FIGS. 8C-D are cross-sectional views depicting additional example embodiments of the medical device.

FIGS. 8A-C depict perspective views of additional example embodiments of medical device 101, where imaging device 102 has a planar or sheet-like layout. In these embodiments, imaging device 102 is an array of six imaging elements 110 arranged symmetrically in a hexagonal pattern to form a distal planar imaging surface 420, although any number of elements 110 in any shape or pattern can be used. To image, ultrasound energy can be transmitted and received from surface 420 in direction 421, which can be any direction within imaging field 430. The dimensions of imaging field 430 can be set to any extent desired in accordance with the needs of the application.

Each element 110 is preferably coupled with the adjacent elements 110 by coupling member 150. In this embodiment, coupling member 150 is a thin, flexible material adapted to allow adjustment of imaging device 102 from the deployed layouts depicted in FIGS. 8A-B to an undeployed layout, such as that depicted in FIGS. 8C-D, and vice versa. FIG. 8A is a perspective view depicting an example embodiment of medical device 101 taken from a position distal to imaging device 102. Distal end 422 of shaft 106 is located at the center of imaging device 102 and can be coupled with each element 110 by flexible coupling member 150. Distal end 422 can also have a transducer element 110 located thereon if desired.

FIG. 8B is a perspective view depicting an example embodiment of medical device 101 taken from a position proximal to imaging device 102. Here, multiple bias devices 426 are depicted coupled with proximal surface 424 of imaging device 102. Bias devices 426 apply a bias, or force, between shaft 106 and imaging device 102 to cause imaging device 102 to unfold into the deployed layout. FIG. 8C depicts an example embodiment of medical device 101 from a position distal to distal end 108 and shows imaging device 102 in the undeployed layout within lumen 105. Here, imaging device 102 is folded up to reduce the width 432, or overall cross-sectional area of imaging device 102 as compared to the deployed layout. In this embodiment, elements 110 are semi-rigid such that they maintain their general shape when adjusted between the deployed and undeployed layouts. Flexible coupling members 150 preferably incur most of the deformation that occurs during adjustment.

Figure 8D:
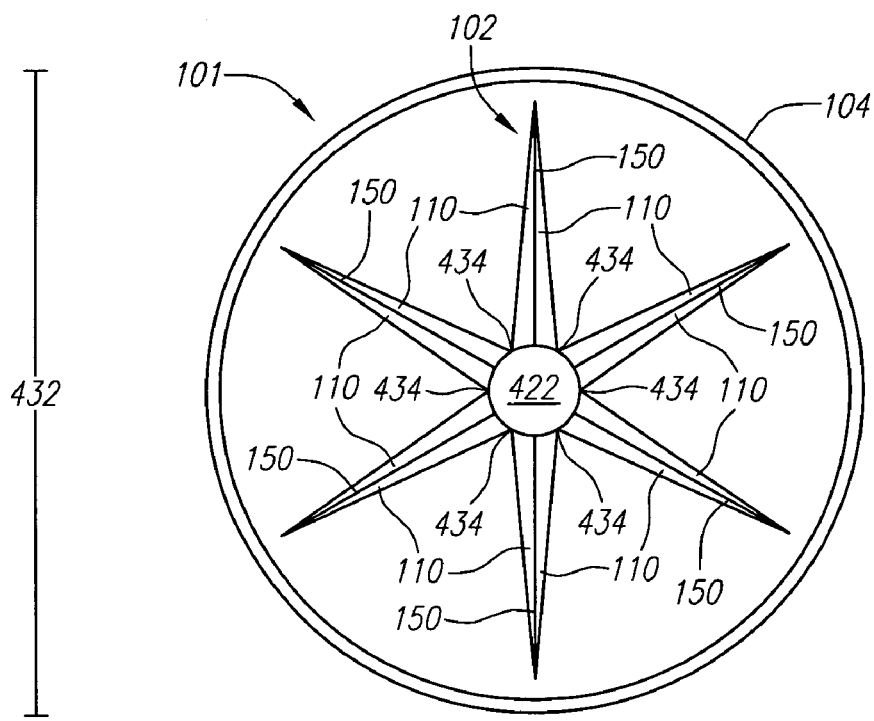

FIG. 8D depicts another example embodiment of medical device 101 where both elements 110 and coupling members 150 are flexible and capable of folding and unfolding, similar to an umbrella. In this embodiment, elements 110 fold along axes 434, which are also depicted in FIG. 8A. Although preferably used in the various embodiments, for ease of illustration, membrane 402 is not shown in FIGS. 8A-D.

Figure 8E:
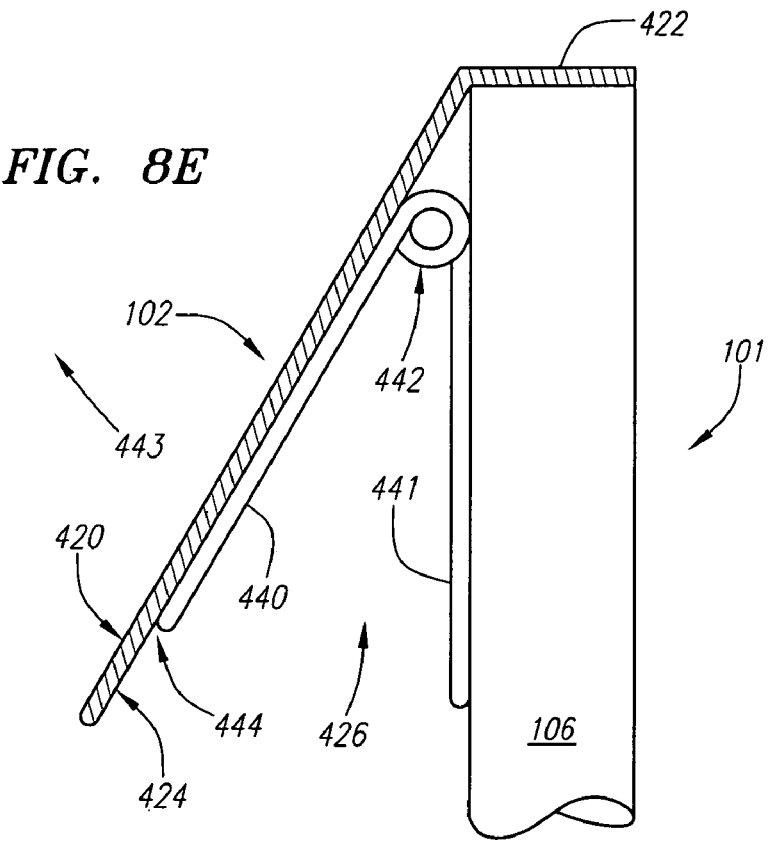
FIGS. 8E-F are cross-sectional views depicting additional example embodiments of a portion of the medical device.
Figure 8F:
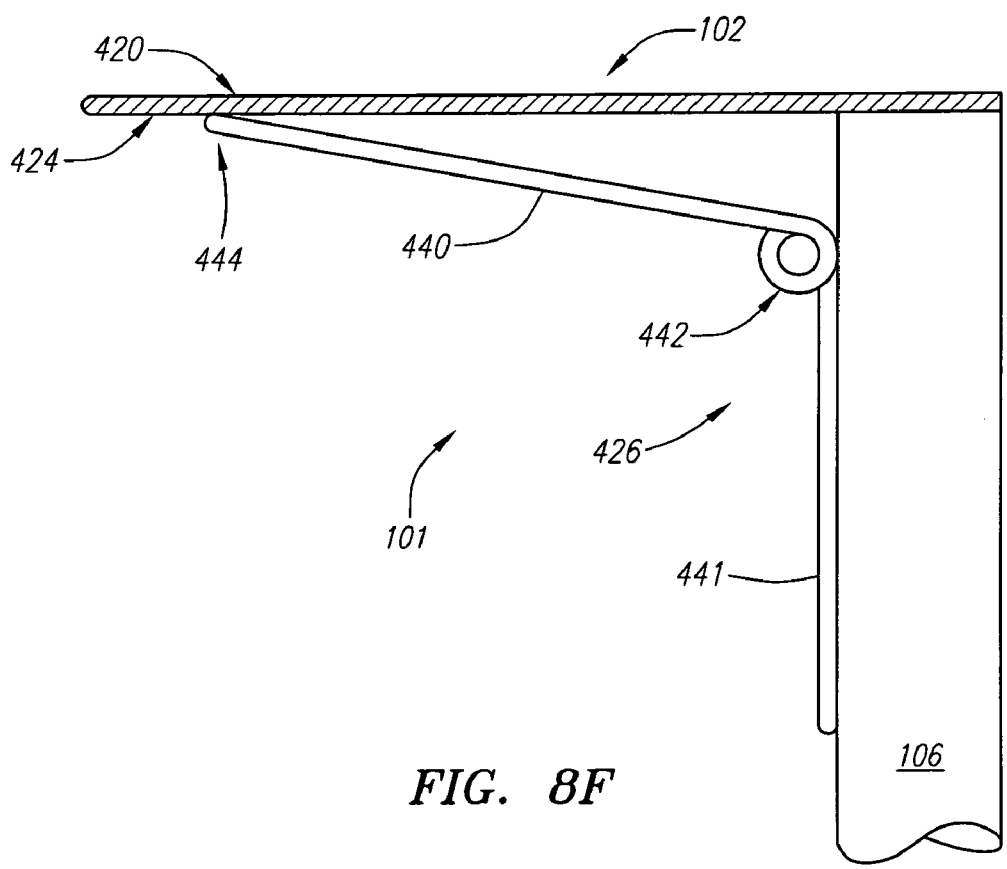

Bias device 426 can be configured in any manner desired to deploy imaging device 102. FIGS. 8E-F are partial cross-sectional views depicting example embodiments of bias device 426 implemented within one portion of medical device 101. Here, bias device 426 is a spring loaded lever having first and second lever members 440 and 441, respectively, with spring 442 coupled therebetween. FIG. 8E depicts bias member 426 in a folded, or relatively compressed, position and FIG. 8F depicts bias member 428 in an unfolded, or relatively expanded, position. First lever member 440 is preferably coupled with proximal surface 424 of imaging device 102 at location 444 and second lever member 441 is positioned against or coupled with shaft 106. Spring 442 applies a bias between each lever member 440 and 441 such that when imaging device 102 is advanced from within lumen 105, first lever member 440 is translated distally in direction 443 from the folded position to the unfolded position causing imaging device 102 to deploy.

Also depicted in FIGS. 8A-B are retraction members 429, which are preferably used to retract imaging device 102 from the deployed position back to the undeployed position after the imaging procedure is complete. Retraction members 429 can be coupled directly to surface 424 of imaging device 102 or to first lever member 440 at locations 428. The distance of location 428 from shaft 106 can vary, but preferably location 428 is in proximity with outer edge 439 to allow a relatively higher amount of leverage to be placed on imaging device 102 to overcome the force applied by bias device 426. Retraction member 429 is preferably coupled with surface 424 or member 440 using a movable coupling such as a hinge or a flexible adhesive or any other coupling that allows the orientation of retraction member 429 with respect to imaging device 102 to change. Preferably, retraction member 429 is a wire, which can be routed through inner lumen 105 and made accessible at the proximal end of elongate sheath 104. By applying a force to retraction members 429 in a proximal direction, a user can overcome the bias applied by bias devices 426 and adjust imaging device 102 to the undeployed layout.

Figure 9A:
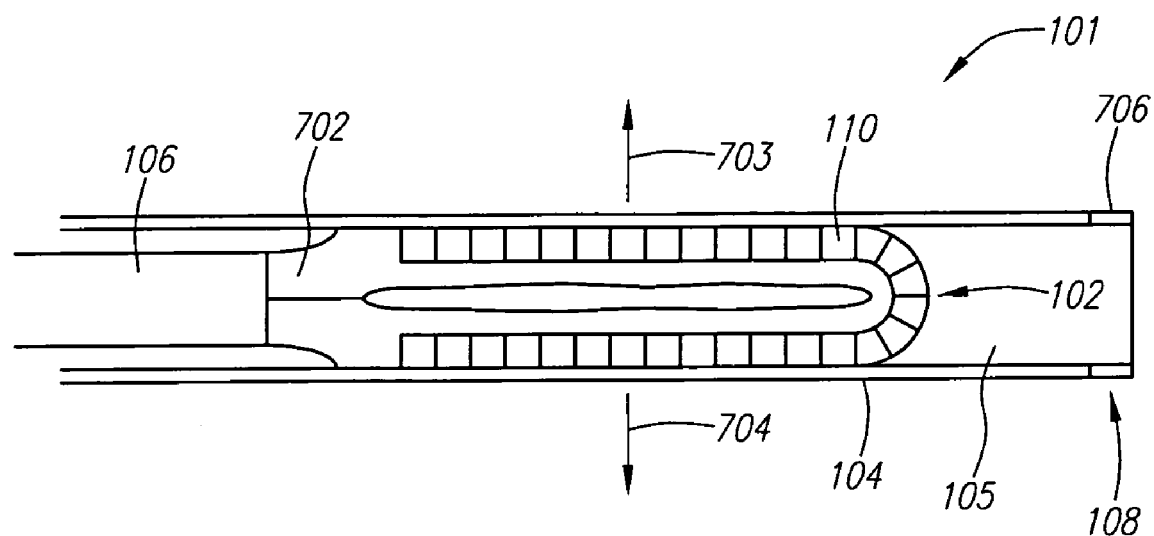
FIG. 9A is a cross-sectional view depicting an additional example embodiment of the medical device.
Figure 9B:
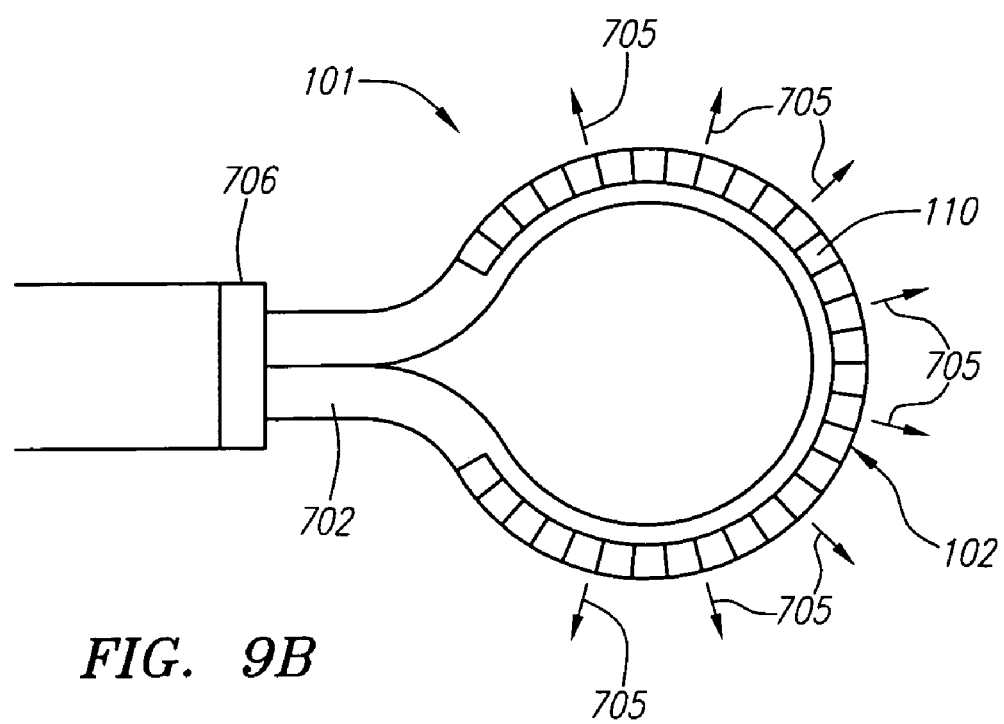
FIG. 9B is a perspective view depicting an additional example embodiment of the medical device.

FIGS. 9A-B depict schematic views of additional example embodiments of medical device 101, where imaging device 102 is adapted to image from an annular, or ring-like base structure 702. FIG. 9A depicts imaging device 102 in an undeployed layout within lumen 105. Here, imaging device 102 is one continuous array of elements 110, although multiple separate arrays can be employed. Elements 110 are coupled with base structure 702 and positioned to image in directions 703 and 704 while imaging device 102 is in the undeployed layout. Base structure 702 can be coupled with distal end of shaft 106 (as shown) or integrally formed with shaft 106 such that shaft 104 and base structure 702 are one unit.

Base structure 702 is preferably formed from a shape memory material and biased towards an annular layout. Communication between the image processing system and the various elements 110 is provided by signal lines (not shown) routed within base structure 702. These signal lines can be coupled with elements 110 in any suitable manner, such as with a conventional bonding technique. Base structure 702 can also be coated with a conductive metallic coating for providing a ground to the various elements 110.

While in the undeployed layout depicted in FIG. 9A, sheath 104 holds base structure 702 in a relatively straightened or closed state. Upon deployment from sheath 104, the restraining force applied by the walls of sheath 104 is removed and base structure 702 is free to adjust to the annular layout. FIG. 9B depicts base structure 702 after being advanced distally from within lumen 105. When in the annular layout, elements 110 are arranged in a convex fashion along base structure 702 and can be used to image in multiple directions, such as outward directions 705. After the imaging procedure is completed, imaging device 102 can be proximally retreated into inner lumen 105 and adjusted to the relatively straightened layout. To facilitate the retraction and compression of base structure 702 back to the undeployed layout, a rigid distal tip 706 can be positioned at distal end 108 of elongate sheath 104. Rigid distal tip 706 preferably acts as a brace forcing imaging device 102 into the relatively straightened layout as device 102 is retreated into lumen 105.

Figure 10A:
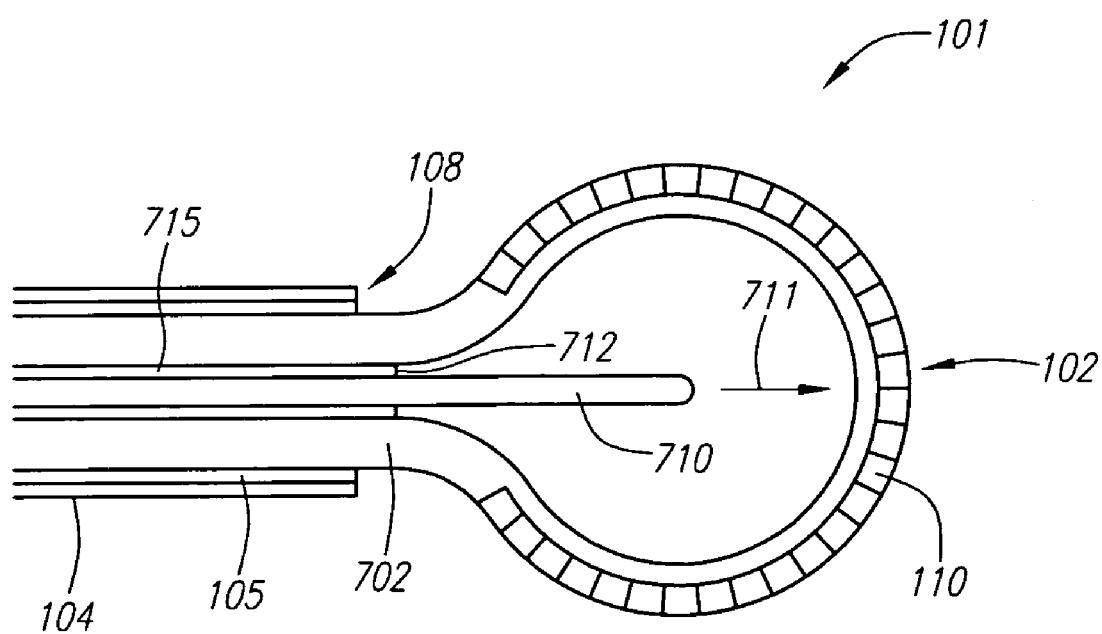
FIG. 10A is a cross-sectional view depicting an additional example embodiment of the medical device.
Figure 10B:
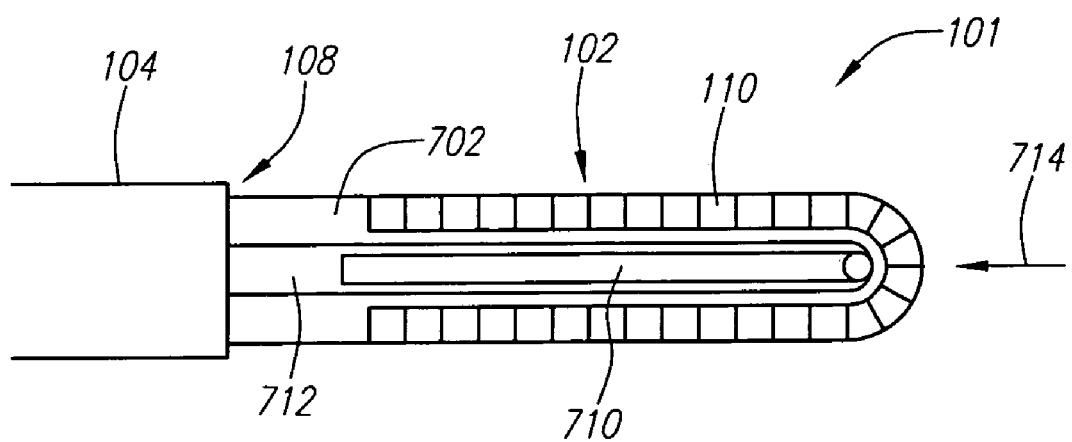
FIG. 10B is a perspective view depicting an additional example embodiment of the medical device.

FIGS. 10A-B depict additional example embodiments of medical device 101 with base structure 702 biased towards an annular layout. Here, the layout of base structure 702 is adjusted with the aid of pusher member 710. FIG. 10A depicts an example embodiment of imaging device 102 in a deployed layout outside of sheath 104. In order to retract base structure 702, pusher member 710 is advanced distally in direction 711 against base structure 702 to cause base structure 702 to collapse into the relatively straightened layout, as depicted in FIG. 10B. Once in the relatively straightened layout, imaging device 102 can be retreated proximally in direction 714 into lumen 105.

Likewise, prior to deployment, pusher member 710 is preferably forced against base structure 702 in direction 711 to maintain base structure 702 in the relatively straightened layout. To deploy imaging device 102, base structure 702 is preferably advanced distally from within sheath 104 while pusher member 710 is used to maintain base structure 702 in the relatively straightened layout. Once advanced to the desired position, pusher member 710 can be retreated proximally to allow base structure 702 to adjust to the annular layout.

In this embodiment, pusher member 710 is slidable within elongate tubular member 712 having inner lumen 715. Tubular member 712 can be coupled with sheath 104, shaft 106 or base structure 702 (as shown). Tubular member 712 is preferably flexible and can be composed of any material in accordance with the needs of the application. The proximal end (not shown) of pusher member 710 is preferably accessible by the user to allow manual or automated manipulation of pusher member 710. Although not shown in FIGS. 9A-B and 10A-B, membrane 402 is preferably coupled with distal end 108 and used during the imaging procedure.

Figure 11A:
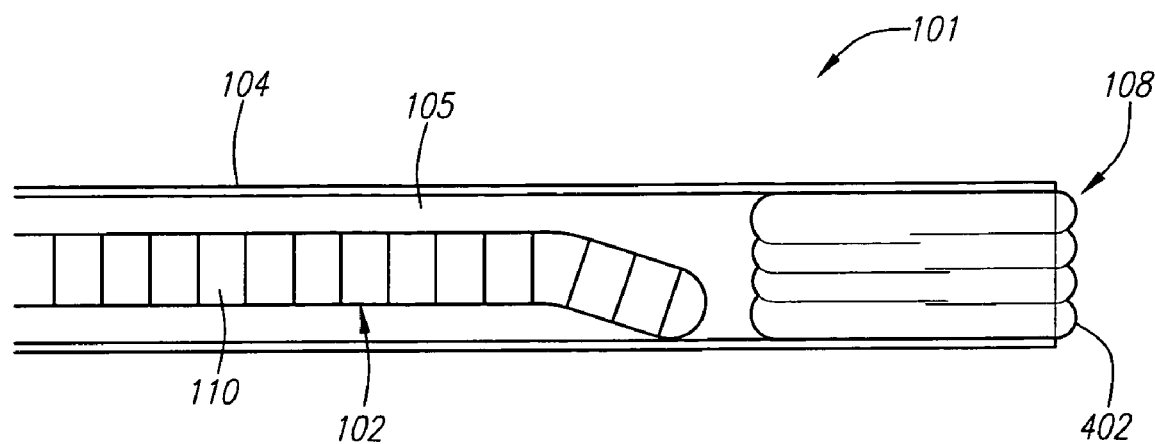
FIG. 11A is a cross-sectional view depicting an additional example embodiment of the medical device.
Figure 11B:
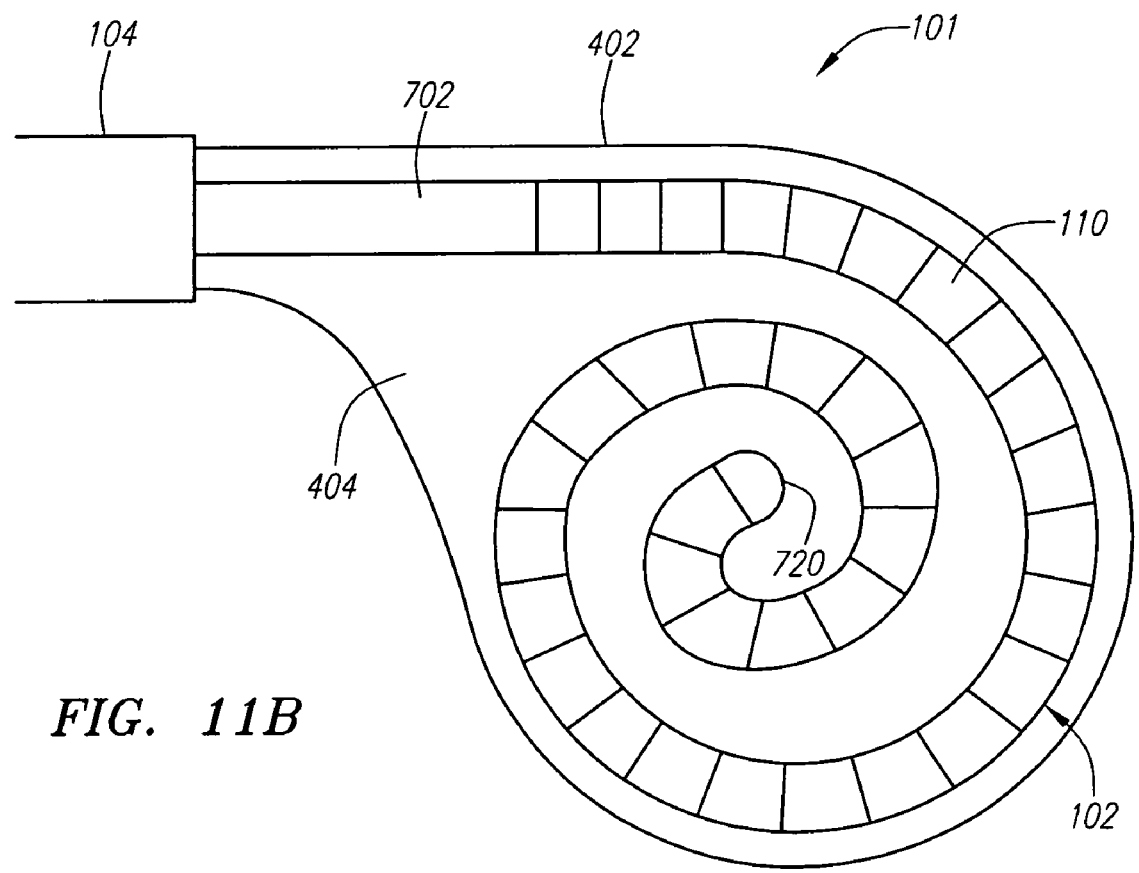
FIG. 11B is a perspective view depicting an additional example embodiment of the medical device.

FIGS. 11A-B depict schematic views of additional example embodiments of medical device 101 where imaging device 102 is adapted to image from a coiled base structure 702. As in previous embodiments, imaging device 102 can include one or more transducer elements 110 arranged continuously (as shown) along base structure 702 or in spaced apart groups. Elements 110 can be arranged in a single row, as depicted in FIGS. 11A-B, or in multiple rows or in any other desired pattern. Base structure 702 is preferably an elongate member composed of a shape memory material and biased towards a coiled layout.

FIG. 11A depicts imaging device 102 in the undeployed layout within lumen 105. While in this layout, the walls of sheath 104 restrain base structure 702 such that it maintains a relatively straightened layout. Once advanced from sheath 104, base structure 702 is free from the restraint and adjusts into the biased, coiled layout as depicted in FIG. 11B. Similar to the previous embodiments, although imaging device 102 can image in both the undeployed and deployed layouts, imaging device 102 has a larger imaging aperture in the deployed layout than in the undeployed layout, which allows imaging device 102 to image a larger imaging field. Base structure 702 can be coupled to the distal end of the shaft 104 by an adhesive, welding or the like or by mechanical coupling members such as a clamp and the like.

In FIG. 11B, membrane 402 is configured such that imaging device 102 is positioned generally in the center of operating spatial region 404 while in the deployed position. Here, membrane 402 has a predetermined shape corresponding to that of imaging device 102 in the deployed position. Membrane 402 can have any shape as desired to accommodate the differing layouts of imaging device 102.

Figure 12:
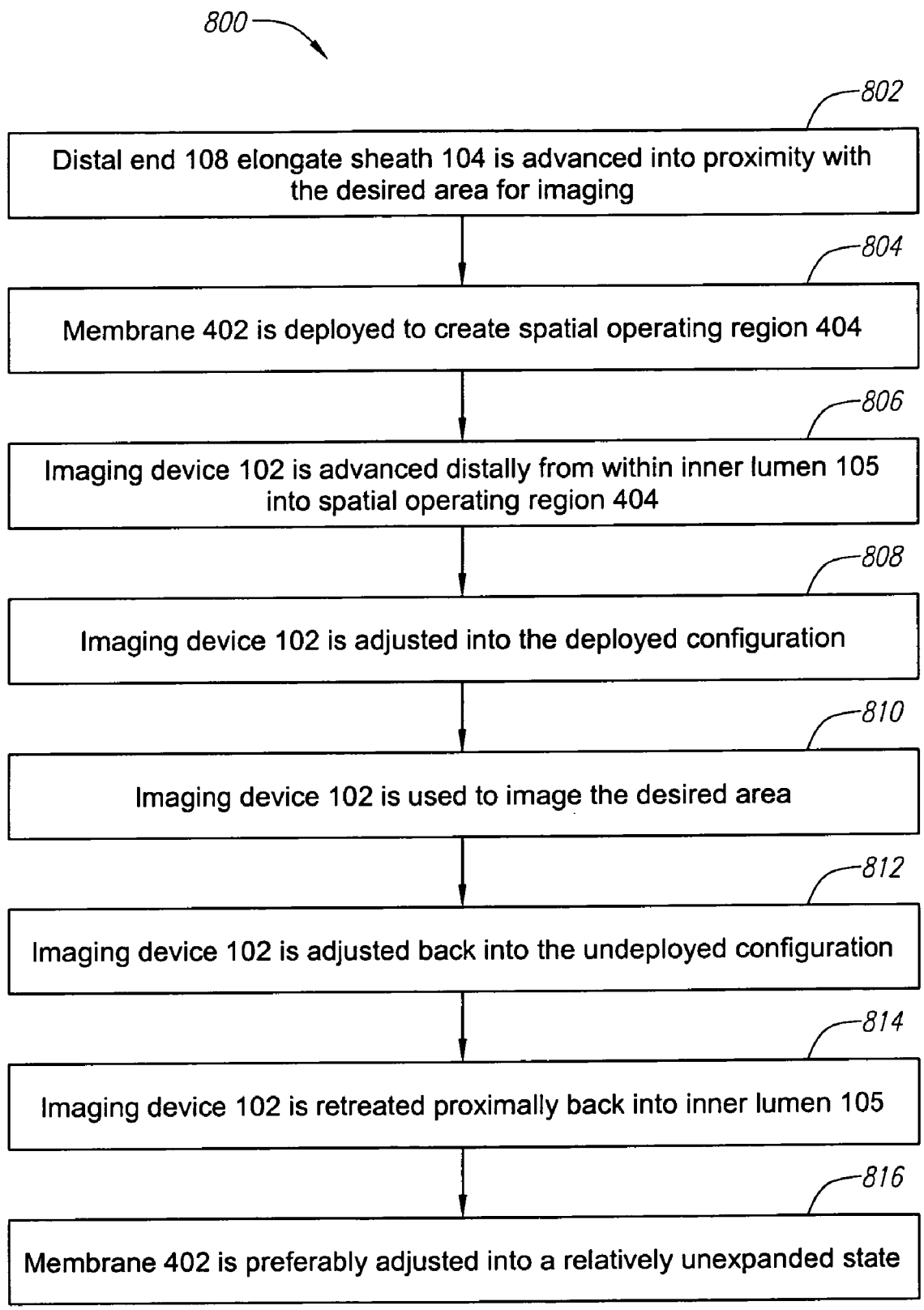
FIG. 12 is a flow diagram depicting an example method of imaging with an example embodiment of the imaging system.

FIG. 12 depicts an example method 800 for imaging with the systems and methods described herein. At 802, distal end 108 of elongate sheath 104 is advanced into proximity with a desired region within the body for imaging. At 804, membrane 402 is deployed to create spatial operating region 404, using expansion members 506, an inflation medium or any other expansion technique desired. Then, at 806, imaging device 102 is advanced distally from within inner lumen 105 into spatial operating region 404 and, at 808, imaging device 102 is adjusted into the deployed layout. Next, at 810, imaging device 102 is used to image the desired region. Once the imaging procedure at 810 is complete, imaging device 102 is adjusted back into the undeployed layout at 812. Then, at 814, imaging device 102 is retreated proximally back into inner lumen 105. In the alternative, 812 and 914 can be combined so that retreating imaging device 102 also adjusts imaging device 102 to the undeployed layout at the same time. Finally, at 816, membrane 402 is preferably adjusted into a relatively unexpanded state, remaining in a deployed position or being retreated proximally into lumen 105.

If one or more expansion members 506 are used to deploy membrane 402, then members 506 are preferably retreated back into inner lumen 105. Preferably, membrane 402 is coupled with the one or more expansion members 506 such that membrane 402 will also be drawn back into lumen 105. However, this is not necessary, as membrane 402 can be left in an unexpanded, deployed state while medical device 101 is withdrawn from the patient. Alternatively, if membrane 402 is deployed using an inflation medium, the inflation medium can be withdrawn from spatial region 404 causing membrane 402 to deflate. Depending, for instance, on the size of lumen 105 and shape of membrane 402, this deflation may or may not retract membrane 402 back into lumen 105. Again, however, retraction of membrane 402 is not necessary and medical device 101 can be withdrawn from the body with membrane 402 in a deflated, deployed state.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A medical ultrasound imaging system for imaging the interior of a living being, comprising:
   an elongate shaft member;
   an elongate tubular member configured for insertion into a living being, the elongate tubular member having an inner lumen adapted to slidably receive the elongate shaft member; and
   an imaging device coupled with the shaft member, the imaging device comprising at least one ultrasound imaging transducer element adjustable from a first layout to a second layout, wherein the at least one ultrasound imaging transducer element is foldable between the first layout and the second layout, wherein the second layout is a planar layout, and wherein the at least one ultrasound imaging transducer element is adapted to image a first imaging field in the first layout and a second imaging field in the second layout, the second imaging field being larger than the first imaging field.

2. The system of claim 1, wherein the at least one ultrasound imaging transducer element is insertable into the inner lumen in the first layout.

3. The system of claim 1, wherein the at least one ultrasound imaging transducer element has a first width in the first layout and a second width in the second layout, the second width being larger than the first width.

4. The system of claim 3, wherein the elongate tubular member has a width larger than the first width of the first layout and smaller than the width of the second layout.

5. The system of claim 1, wherein the at least one ultrasound imaging transducer element has a first aperture in the first layout and a second aperture in the second layout, the second aperture being larger than the first.

6. The system of claim 1, wherein the at least one ultrasound imaging transducer element is two dimensional.

7. The system of claim 1, wherein the at least one ultrasound imaging transducer element is adjustable using an electrostatic force.

8. The system of claim 7, wherein the at least one ultrasound imaging transducer element comprises a first electrode and a second electrode, the first and second electrodes being located such that the electrostatic force applied between the first and second electrodes is operable to adjust the at least one ultrasound imaging transducer element from the first layout to the second layout.

9. The system of claim 7, wherein the imaging device further comprises a first electrode and a second electrode, the first and second electrodes being located such that the electrostatic force applied between the first and second electrodes is operable to adjust the at least one ultrasound imaging transducer element from the second layout to the first layout.

10. The system of claim 1, further comprising a bias member coupled with the imaging device and adapted to adjust the at least one ultrasound imaging transducer element from the first layout to the second layout.

11. The system of claim 1, further comprising an elongate wire member coupled with the imaging device and adapted to adjust the at least one ultrasound imaging transducer element.

12. The system of claim 1, further comprising an image processing system communicatively coupled with the imaging device and adapted to process image data from the at least one ultrasound imaging transducer element.

13. The system of claim 1, wherein the imaging device further comprises:
first and second base structures, each base structure having a planar surface;
a first ultrasound imaging transducer element on the planar surface of the first base structure;
a second ultrasound imaging transducer element on the planar surface of the second base structure; and
a coupling member coupled between the first base structure and the second base structure, wherein the at least one ultrasound imaging transducer element is foldable about the coupling member.

14. The system of claim 13, wherein the first ultrasound imaging transducer element and second ultrasound imaging transducer element image in substantially opposite directions in the first layout and image in substantially the same direction in the second layout.

15. The system of claim 13, wherein the first and second base structures are stacked in the first layout and are arranged side-by-side in the second layout.

16. A medical ultrasound imaging system for imaging the interior of a living being comprising:
an elongate shaft member;
an elongate tubular member configured for insertion into a living being, the member having an inner lumen adapted to slidably receive the elongate shaft member;
an imaging device coupled with the shaft member, the imaging device comprising at least one ultrasound imaging transducer element adjustable from a first layout to a second layout, wherein the at least one ultrasound imaging transducer element is adapted to image a first imaging field in the first layout and a second imaging field in the second layout, the second imaging field being larger than the first imaging field; and
a flexible membrane located on the distal end of the elongate tubular member, wherein the membrane is inflatable to an expanded state having a larger width than the elongate tubular member, and the membrane is adapted to slidably receive the at least one ultrasound imaging transducer element therein in the expanded state and to enclose the at least one ultrasound imaging transducer element therein when the at least one ultrasound imaging transducer element is adjusted to the second layout.

17. The system of claim 16, further comprising an expansion member adapted to expand the membrane.

18. The system of claim 16, wherein the first layout is a relatively straight layout and the second layout is a coiled layout.

19. The system of claim 16, wherein the first layout is a relatively straight layout and the second layout is an annular layout.

20. The system of claim 19, further comprising an elongate pusher member adapted to push a distal region of the imaging device in a distal direction to adjust the at least one ultrasound imaging transducer element from the second layout to the first layout.

21. The system of claim 16, wherein the second layout is an umbrella-like layout.

22. The system of claim 16, wherein the at least one ultrasound imaging transducer element comprises a shape memory material biased towards the second layout.

23. A method of medical imaging, comprising:
positioning a medical device within a living being, wherein the medical device comprises an imaging device, wherein the imaging device comprises at least one ultrasound imaging transducer element that is foldable from an undeployed layout to a deployed layout, wherein the deployed layout is a planar layout;
imaging the living being with the at least one ultrasound imaging transducer element in the undeployed layout;
adjusting the at least one ultrasound imaging transducer element to the deployed layout; and
imaging the living being with the at least one ultrasound imaging transducer element in the deployed layout.

24. The method of claim 23, wherein the at least one ultrasound imaging transducer element has a relatively larger aperture in the deployed layout than in the undeployed layout.

25. The method of claim 23, wherein the at least one ultrasound imaging transducer element is adapted to image a relatively larger imaging field in the deployed layout than in the undeployed layout.

26. The method of claim 23, wherein the medical device comprises:
an elongate sheath having an inner lumen; and
an elongate shaft coupled with the imaging device and adapted to slide within the inner lumen.

27. The method of claim 23, further comprising unfolding the at least one ultrasound imaging transducer element with an electrostatic force.

28. A method of medical imaging, comprising:
positioning a medical device within a living being, wherein the medical device comprises an imaging device, the imaging device comprising at least one ultrasound imaging transducer element, wherein the medical device also comprises an elongate sheath having an inner lumen adapted to slidably receive the at least one ultrasound imaging transducer element, and an inflatable membrane located at a distal end of the elongate sheath;
imaging the living being with the at least one ultrasound imaging transducer element in an undeployed layout;
inflating the membrane to define a spatial operating region for the at least one ultrasound imaging transducer element;
advancing the at least one ultrasound imaging transducer element into the inflated membrane;
adjusting the at least one ultrasound imaging transducer element to a deployed layout within the inflated membrane; and
imaging the living being with the at least one ultrasound imaging transducer element in the deployed layout.

29. The method of claim 28, wherein the imaging device is coupled with a base structure adapted to adjust the at least one ultrasound imaging transducer element into the deployed layout as the at least one ultrasound imaging transducer element is advanced into the inflated membrane.

30. The method of claim 28, wherein the membrane is a first portion of the elongate sheath having a flexibility relatively greater than a second, adjacent portion of the elongate sheath.

31. The method of claim 28, further comprising
retreating the at least one ultrasound imaging transducer element into the sheath.

32. The method of claim 28, wherein adjusting the at least one ultrasound imaging transducer element comprises coiling the at least one ultrasound imaging transducer element from a relatively straight, undeployed layout to a coiled, deployed layout.

33. The method of claim 28, wherein adjusting the at least one ultrasound imaging transducer element comprises expanding the at least one ultrasound imaging transducer element from a relatively straight, undeployed layout to an annular, deployed layout.

34. The method of claim 28, further comprising adjusting the at least one ultrasound imaging transducer element from the deployed layout to the undeployed layout prior to imaging the living being with the at least one ultrasound imaging transducer element in the undeployed layout.

35. A medical imaging system, comprising:
an elongate sheath having an inner lumen and a distal end;
an elongate shaft;
an imaging device adjustable between an undeployed and a deployed layout, the imaging device comprising at least one ultrasound imaging transducer element coupled with the elongate shaft and adapted to slide within the inner lumen when in the undeployed layout, wherein the at least one ultrasound imaging transducer element is adapted to image a first imaging field in the undeployed layout and a second imaging field in the deployed layout, the second imaging field being larger than the first imaging field; and
a flexible membrane coupled with the distal end of the elongate sheath, wherein the flexible membrane is deployable from the distal end of the elongate sheath and inflatable to define a spatial operating region for the at least one ultrasound imaging transducer element, wherein the flexible membrane is adapted to slidably receive the at least one ultrasound imaging transducer element therein and to enclose the at least one ultrasound imaging transducer element when the at least one ultrasound imaging transducer element is adjusted to the deployed layout.

36. The medical imaging system of claim 35, wherein the deployed layout of the at least one ultrasound imaging transducer element has a width that is greater than the width of the elongate sheath.

37. The medical imaging system of claim 35, further comprising an image processing system adapted to control the imaging device and process an output signal received from the imaging device, the output signal being representative of an area imaged by the at least one ultrasound imaging transducer element.

38. The medical imaging system of claim 37, wherein the image processing system is further adapted to control the adjustment of the at least one ultrasound imaging transducer element.

\* \* \* \* \*